(12) United States Patent
Buhler et al.

(10) Patent No.: US 10,957,423 B2
(45) Date of Patent: *Mar. 23, 2021

(54) METHOD AND APPARATUS FOR PERFORMING SIMILARITY SEARCHING

(71) Applicant: Washington University, St. Louis, MO (US)

(72) Inventors: Jeremy Daniel Buhler, St. Louis, MO (US); Roger Dean Chamberlain, St. Louis, MO (US); Mark Allen Franklin, St. Louis, MO (US); Kwame Gyang, St. Louis, MO (US); Arpith Chacko Jacob, St. Louis, MO (US); Praveen Krishnamurthy, St. Louis, MO (US); Joseph Marion Lancaster, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/804,847

(22) Filed: Feb. 28, 2020

(65) Prior Publication Data
US 2020/0251185 A1 Aug. 6, 2020

Related U.S. Application Data

(60) Continuation of application No. 15/403,687, filed on Jan. 11, 2017, now Pat. No. 10,580,518, which is a division of application No. 13/969,935, filed on Aug. 19, 2013, now Pat. No. 9,547,680, which is a division of application No. 13/046,395, filed on Mar. 11, 2011, now Pat. No. 8,515,682, which is a division of application No. 11/359,285, filed on Feb. 22, 2006, now Pat. No. 7,917,299.

(60) Provisional application No. 60/658,418, filed on Mar. 3, 2005, provisional application No. 60/736,081, filed on Nov. 11, 2005.

(51) Int. Cl.
*G16B 50/00* (2019.01)
*G06F 16/22* (2019.01)
*G16B 30/00* (2019.01)

(52) U.S. Cl.
CPC ......... *G16B 50/00* (2019.02); *G06F 16/2255* (2019.01); *G16B 30/00* (2019.02)

(58) Field of Classification Search
CPC ........ G06N 3/08; G06N 3/0445; G06N 3/063; G06N 20/00; G06N 3/04; G06N 3/02; G06N 3/0454; G06N 5/025; G06N 7/005; H04L 9/3239; H04L 67/12; H04L 9/0643; H04L 63/0245; H04L 65/102; H04L 2209/122; H04L 9/0869; H04L 9/14; G06F 21/76; G06F 30/331; G06F 16/2455; G06F 16/90335; G06F 17/00; G06F 11/302; G06F 17/10; G06F 9/3867; G06F 9/4401; G06K 9/6257; G06K 9/6201; G06K 9/6202; G06K 9/6263; G16H 40/63; G16H 10/40; G16H 50/20; C12Q 1/68; G16B 30/00; G16B 30/10; G16B 40/00; G16B 50/00; G16B 5/20; G16B 99/00

See application file for complete search history.

(56) References Cited

U.S. PATENT DOCUMENTS

| | | |
|---|---|---|
| 3,601,808 A | 8/1971 | Vlack |
| 3,611,314 A | 10/1971 | Pritchard, Jr. et al. |
| 3,729,712 A | 4/1973 | Glassman |
| 3,824,375 A | 7/1974 | Gross et al. |
| 3,848,235 A | 11/1974 | Lewis et al. |
| 3,906,455 A | 9/1975 | Houston et al. |
| 4,081,607 A | 3/1978 | Vitols et al. |
| 4,300,193 A | 11/1981 | Bradley et al. |

(Continued)

FOREIGN PATENT DOCUMENTS

| | | |
|---|---|---|
| EP | 0880088 | 11/1996 |
| EP | 0851358 A | 7/1998 |

(Continued)

OTHER PUBLICATIONS

Dharmapurikar et al., "Robust TCP Stream Reassembly in the Presence of Adversaries", Proc. of the 14th Conference on USENIX Security Symposium—vol. 14, 16 pages, Baltimore, MD, 2005; http://www.icir.org/vern/papers/TcpReassembly/TCPReassembly.pdf.

(Continued)

*Primary Examiner* — Mary K Zeman
(74) *Attorney, Agent, or Firm* — Thompson Coburn LLP

(57) ABSTRACT

Apparatuses and methods are disclosed for comparing a first biosequence string with a second biosequence string to assess similarity between those biosequence strings. For example, a field programmable gate array (FPGA) can be used to (1) detect substrings of the second biosequence string that are matches to substrings of the first biosequence string, and (2) map the detected substrings of the second biosequence string to corresponding positions in the first biosequence string where the detected substrings are located based on a data structure that links substrings of the first biosequence string to positions in the first biosequence string where the substrings of the first biosequence string are located. These operations can be used to seed an alignment between the first and second biosequence strings that permits comparisons to be performed over longer substrings of the first and second biosequence strings so that similarities between those longer substrings can be quantified.

30 Claims, 23 Drawing Sheets

(56) References Cited

U.S. PATENT DOCUMENTS

| | | |
|---|---|---|
| 4,314,356 A | 2/1982 | Scarbrough |
| 4,464,718 A | 8/1984 | Dixon et al. |
| 4,550,436 A | 10/1985 | Freeman et al. |
| 4,811,210 A | 3/1989 | McAulay |
| 4,811,214 A | 3/1989 | Nosenchuck et al. |
| 4,823,306 A | 4/1989 | Barbic et al. |
| 5,050,075 A | 9/1991 | Herman et al. |
| 5,101,424 A | 3/1992 | Clayton et al. |
| 5,140,692 A | 8/1992 | Morita |
| 5,208,491 A | 5/1993 | Ebeling et al. |
| 5,226,165 A | 7/1993 | Martin |
| 5,233,539 A | 8/1993 | Agrawal et al. |
| 5,243,655 A | 9/1993 | Wang |
| 5,249,292 A | 9/1993 | Chiappa |
| 5,265,065 A | 11/1993 | Turtle |
| 5,319,776 A | 6/1994 | Hile et al. |
| 5,339,411 A | 8/1994 | Heaton, Jr. |
| 5,347,634 A | 9/1994 | Herrell et al. |
| 5,361,373 A | 11/1994 | Gilson |
| 5,371,794 A | 12/1994 | Diffie et al. |
| 5,388,259 A | 2/1995 | Fleischman et al. |
| 5,404,411 A | 4/1995 | Banton et al. |
| 5,418,951 A | 5/1995 | Damashek |
| 5,421,028 A | 5/1995 | Swanson |
| 5,440,723 A | 8/1995 | Arnold et al. |
| 5,461,712 A | 10/1995 | Chelstowski et al. |
| 5,463,701 A | 10/1995 | Kantner, Jr. et al. |
| 5,465,353 A | 11/1995 | Hull et al. |
| 5,481,735 A | 1/1996 | Mortensen et al. |
| 5,497,488 A | 3/1996 | Akizawa et al. |
| 5,517,642 A | 5/1996 | Bezek et al. |
| 5,535,384 A | 7/1996 | Kasahara |
| 5,544,352 A | 8/1996 | Egger |
| 5,546,578 A | 8/1996 | Takada et al. |
| 5,596,569 A | 1/1997 | Madonna et al. |
| 5,680,634 A | 10/1997 | Estes |
| 5,684,980 A | 11/1997 | Casselman |
| 5,687,297 A | 11/1997 | Coonan et al. |
| 5,701,464 A | 12/1997 | Aucsmith |
| 5,712,942 A | 1/1998 | Jennings et al. |
| 5,721,898 A | 2/1998 | Beardsley et al. |
| 5,781,772 A | 7/1998 | Wilkinson, III et al. |
| 5,785,636 A | 7/1998 | Bonander et al. |
| 5,802,290 A | 9/1998 | Casselman |
| 5,805,832 A | 9/1998 | Brown |
| 5,813,000 A | 9/1998 | Furlani |
| 5,819,273 A | 10/1998 | Vora et al. |
| 5,826,075 A | 10/1998 | Bealkowski et al. |
| 5,886,701 A | 3/1999 | Chauvin et al. |
| 5,913,211 A | 6/1999 | Nitta |
| 5,930,753 A | 7/1999 | Potamianos et al. |
| 5,950,006 A | 9/1999 | Crater et al. |
| 5,950,196 A | 9/1999 | Pyreddy et al. |
| 5,978,801 A | 11/1999 | Yuasa |
| 5,991,881 A | 11/1999 | Conklin et al. |
| 5,995,963 A | 11/1999 | Nanba et al. |
| 6,006,264 A | 12/1999 | Colby et al. |
| 6,023,755 A | 2/2000 | Casselman |
| 6,023,760 A | 2/2000 | Karttunen |
| 6,028,939 A | 2/2000 | Yin |
| 6,034,538 A | 3/2000 | Abramovici |
| 6,044,407 A | 3/2000 | Jones et al. |
| 6,067,569 A | 5/2000 | Khaki et al. |
| 6,073,160 A | 6/2000 | Grantham et al. |
| 6,096,091 A | 8/2000 | Hartmann |
| 6,105,067 A | 8/2000 | Batra |
| 6,134,551 A | 10/2000 | Aucsmith |
| RE36,946 E | 11/2000 | Diffie et al. |
| 6,147,890 A | 11/2000 | Kawana et al. |
| 6,147,976 A | 11/2000 | Shand et al. |
| 6,169,969 B1 | 1/2001 | Cohen |
| 6,175,874 B1 | 1/2001 | Imai et al. |
| 6,178,494 B1 | 1/2001 | Casselman |
| 6,226,676 B1 | 5/2001 | Crump et al. |
| 6,243,753 B1 | 6/2001 | Machin et al. |
| 6,247,060 B1 | 6/2001 | Boucher et al. |
| 6,272,616 B1 | 8/2001 | Fernando et al. |
| 6,279,113 B1 | 8/2001 | Vaidya |
| 6,289,440 B1 | 9/2001 | Casselman |
| 6,317,795 B1 | 11/2001 | Malkin et al. |
| 6,339,819 B1 | 1/2002 | Huppenthal et al. |
| 6,377,942 B1 | 4/2002 | Hinsley et al. |
| 6,381,242 B1 | 4/2002 | Maher, III et al. |
| 6,389,532 B1 | 5/2002 | Gupta et al. |
| 6,397,259 B1 | 5/2002 | Lincke et al. |
| 6,397,335 B1 | 5/2002 | Franczek et al. |
| 6,412,000 B1 | 6/2002 | Riddle et al. |
| 6,430,272 B1 | 8/2002 | Maruyama et al. |
| 6,463,474 B1 | 10/2002 | Fuh et al. |
| 6,499,107 B1 | 12/2002 | Gleichauf et al. |
| 6,578,147 B1 | 6/2003 | Shanklin et al. |
| 6,591,302 B2 | 7/2003 | Boucher et al. |
| 6,625,150 B1 | 9/2003 | Yu |
| 6,691,301 B2 | 2/2004 | Bowen |
| 6,704,816 B1 | 3/2004 | Burke |
| 6,711,558 B1 | 3/2004 | Indeck et al. |
| 6,765,918 B1 | 7/2004 | Dixon et al. |
| 6,772,345 B1 | 8/2004 | Shetty |
| 6,785,677 B1 | 8/2004 | Fritchman |
| 6,801,938 B1 | 10/2004 | Bookman et al. |
| 6,804,667 B1 | 10/2004 | Martin |
| 6,807,156 B1 | 10/2004 | Veres et al. |
| 6,886,103 B1 | 4/2005 | Brustoloni et al. |
| 6,931,408 B2 | 8/2005 | Adams et al. |
| 6,931,545 B1 | 8/2005 | Ta et al. |
| 6,944,168 B2 | 9/2005 | Paatela et al. |
| 6,978,223 B2 | 12/2005 | Milliken |
| 6,980,976 B2 | 12/2005 | Alpha et al. |
| 6,981,054 B1 | 12/2005 | Krishna |
| 7,019,674 B2 | 3/2006 | Cadambi et al. |
| 7,046,848 B1 | 5/2006 | Olcott |
| 7,065,482 B2 | 6/2006 | Shorey et al. |
| 7,089,326 B2 | 8/2006 | Boucher et al. |
| 7,093,023 B2 | 8/2006 | Lockwood et al. |
| 7,127,510 B2 | 10/2006 | Yoda et al. |
| 7,139,743 B2 | 11/2006 | Indeck et al. |
| 7,167,980 B2 | 1/2007 | Chiu |
| 7,181,437 B2 | 2/2007 | Indeck et al. |
| 7,222,114 B1 | 5/2007 | Chan et al. |
| 7,224,185 B2 | 5/2007 | Campbell et al. |
| 7,225,188 B1 | 5/2007 | Gai et al. |
| 7,257,842 B2 | 8/2007 | Barton et al. |
| 7,277,887 B1 | 10/2007 | Burrows et al. |
| 7,305,383 B1 | 12/2007 | Kubesh et al. |
| 7,305,391 B2 | 12/2007 | Wyschogrod et al. |
| 7,363,277 B1 | 4/2008 | Dutta et al. |
| 7,376,755 B2 | 5/2008 | Pandya |
| 7,386,564 B2 | 6/2008 | Abdo et al. |
| 7,408,932 B2 | 8/2008 | Kounavis et al. |
| 7,411,957 B2 | 8/2008 | Stacy et al. |
| 7,415,723 B2 | 8/2008 | Pandya |
| 7,420,931 B2 | 9/2008 | Nanda et al. |
| 7,444,515 B2 | 10/2008 | Dharmapurikar et al. |
| 7,454,418 B1 | 11/2008 | Wang |
| 7,457,834 B2 | 11/2008 | Jung et al. |
| 7,461,064 B2 | 12/2008 | Fontoura et al. |
| 7,467,155 B2 | 12/2008 | McCool et al. |
| 7,478,431 B1 | 1/2009 | Nachenberg |
| 7,480,253 B1 | 1/2009 | Allan |
| 7,487,264 B2 | 2/2009 | Pandya |
| 7,536,462 B2 | 5/2009 | Pandya |
| 7,580,719 B2 | 8/2009 | Karmarkar |
| 7,598,958 B1 | 10/2009 | Kelleher |
| 7,627,693 B2 | 12/2009 | Pandya |
| 7,631,107 B2 | 12/2009 | Pandya |
| 7,636,703 B2 * | 12/2009 | Taylor ............... H04L 63/0245 706/62 |
| 7,680,790 B2 | 3/2010 | Indeck et al. |
| 7,701,945 B2 | 4/2010 | Roesch et al. |
| 7,715,436 B1 | 5/2010 | Eiriksson et al. |
| 7,760,733 B1 | 7/2010 | Eiriksson et al. |
| 7,827,190 B2 | 11/2010 | Pandya |
| 7,831,606 B2 | 11/2010 | Pandya |
| 7,831,607 B2 | 11/2010 | Pandya |

(56) References Cited

U.S. PATENT DOCUMENTS

| | | |
|---|---|---|
| 7,870,217 B2 | 1/2011 | Pandya |
| 7,890,692 B2 | 2/2011 | Pandya |
| 7,899,976 B2 | 3/2011 | Pandya |
| 7,899,977 B2 | 3/2011 | Pandya |
| 7,899,978 B2 | 3/2011 | Pandya |
| 7,912,808 B2 | 3/2011 | Pandya |
| 7,917,299 B2 * | 3/2011 | Buhler ................ G16B 50/00 702/19 |
| 7,930,314 B2 | 4/2011 | Gupta |
| 7,944,920 B2 | 5/2011 | Pandya |
| 7,949,650 B2 | 5/2011 | Indeck et al. |
| 7,953,743 B2 | 5/2011 | Indeck et al. |
| 7,954,114 B2 | 5/2011 | Chamberlain et al. |
| 7,996,348 B2 | 8/2011 | Pandya |
| 8,005,966 B2 | 8/2011 | Pandya |
| 8,027,893 B1 | 9/2011 | Burrows et al. |
| 8,030,888 B2 | 10/2011 | Pandya et al. |
| 8,051,022 B2 | 11/2011 | Pandya |
| 8,055,601 B2 | 11/2011 | Pandya |
| 8,069,102 B2 | 11/2011 | Indeck et al. |
| 8,095,508 B2 * | 1/2012 | Chamberlain .......... G06F 21/76 707/636 |
| 8,131,697 B2 | 3/2012 | Indeck et al. |
| 8,181,239 B2 | 5/2012 | Pandya |
| 8,200,599 B2 | 6/2012 | Pandya |
| 8,260,754 B2 | 9/2012 | Tatebe et al. |
| 8,274,682 B2 | 9/2012 | Parkinson |
| 8,326,819 B2 | 12/2012 | Indeck et al. |
| 8,374,986 B2 | 2/2013 | Indeck et al. |
| 8,515,682 B2 * | 8/2013 | Buhler ............... G16B 16/2255 702/19 |
| 8,549,024 B2 | 10/2013 | Indeck et al. |
| 8,595,104 B2 | 11/2013 | Parsons et al. |
| 8,600,856 B2 | 12/2013 | Parsons et al. |
| 8,601,086 B2 | 12/2013 | Pandya |
| 8,620,881 B2 * | 12/2013 | Chamberlain ........ G06F 21/602 707/693 |
| 8,626,624 B2 | 1/2014 | Parsons et al. |
| 8,655,764 B2 | 2/2014 | Parsons et al. |
| 8,737,606 B2 | 5/2014 | Taylor et al. |
| 8,751,452 B2 * | 6/2014 | Chamberlain .......... G06F 17/00 707/636 |
| 8,762,249 B2 | 6/2014 | Taylor et al. |
| 8,768,805 B2 | 7/2014 | Taylor et al. |
| 8,768,888 B2 * | 7/2014 | Chamberlain ........ G06F 9/4881 707/636 |
| 8,843,408 B2 | 9/2014 | Singla et al. |
| 8,879,727 B2 | 11/2014 | Taylor et al. |
| 8,880,501 B2 | 11/2014 | Indeck et al. |
| 8,983,063 B1 | 3/2015 | Taylor et al. |
| 9,014,989 B2 * | 4/2015 | McMillen .............. G16B 30/00 702/20 |
| 9,020,928 B2 | 4/2015 | Indeck et al. |
| 9,176,775 B2 * | 11/2015 | Chamberlain ....... G06F 16/2455 |
| 9,483,610 B2 * | 11/2016 | McMillen .............. G16B 30/00 |
| 9,519,752 B2 * | 12/2016 | Rooyen ................ H01L 23/528 |
| 9,529,967 B2 * | 12/2016 | Rooyen ................ G06F 13/16 |
| 9,547,680 B2 * | 1/2017 | Buhler .................. G16B 50/00 |
| 9,576,103 B2 * | 2/2017 | McMillen ........... G06F 13/4265 |
| 9,576,104 B2 * | 2/2017 | van Rooyen .......... G16B 40/00 |
| 9,679,104 B2 * | 6/2017 | van Rooyen ....... H01L 27/0207 |
| 9,697,327 B2 * | 7/2017 | McMillen .............. G16B 30/00 |
| 9,792,405 B2 * | 10/2017 | van Rooyen .......... G16B 40/00 |
| 9,858,384 B2 * | 1/2018 | Rooyen ................ H01L 21/768 |
| 9,898,312 B2 | 2/2018 | Chamberlain et al. |
| 9,898,424 B2 * | 2/2018 | van Rooyen ....... G06F 13/4265 |
| 9,916,622 B2 | 3/2018 | Parsons et al. |
| 9,953,132 B2 * | 4/2018 | van Rooyen ..... H01L 21/76886 |
| 9,953,134 B2 * | 4/2018 | van Rooyen ....... G06F 13/4068 |
| 9,953,135 B2 * | 4/2018 | van Rooyen ......... H01L 21/768 |
| 9,990,393 B2 | 6/2018 | Parsons et al. |
| 10,037,568 B2 | 7/2018 | Taylor et al. |
| 10,048,179 B2 * | 8/2018 | Lai ...................... G01N 3/08 |
| 10,062,115 B2 | 8/2018 | Taylor et al. |
| 10,068,054 B2 * | 9/2018 | Van Rooyen .......... G06N 3/002 |
| 10,083,276 B2 * | 9/2018 | van Rooyen ....... G06F 13/4068 |
| 10,121,196 B2 | 11/2018 | Parsons et al. |
| 10,191,974 B2 | 1/2019 | Indeck et al. |
| 10,210,308 B2 * | 2/2019 | van Rooyen .......... G16B 30/00 |
| 10,216,898 B2 * | 2/2019 | McMillen ........... G06F 13/4068 |
| 10,229,453 B2 | 3/2019 | Taylor et al. |
| 10,262,105 B2 * | 4/2019 | van Rooyen .......... G16B 40/00 |
| 10,572,824 B2 | 2/2020 | Chamberlain et al. |
| 10,580,518 B2 * | 3/2020 | Buhler ................ G06F 16/2255 |
| 10,622,096 B2 * | 4/2020 | van Rooyen .......... G16B 30/00 |
| 10,691,775 B2 * | 6/2020 | van Rooyen .......... G16B 50/00 |
| 2001/0003193 A1 | 6/2001 | Woodring et al. |
| 2001/0004354 A1 | 6/2001 | Jolitz |
| 2001/0013048 A1 | 8/2001 | Imbert de Tremiolles et al. |
| 2001/0014093 A1 | 8/2001 | Yoda et al. |
| 2001/0025315 A1 | 9/2001 | Jolitz |
| 2001/0041012 A1 | 11/2001 | Hsieh et al. |
| 2001/0052038 A1 | 12/2001 | Fallon et al. |
| 2001/0056547 A1 | 12/2001 | Dixon |
| 2002/0010825 A1 | 1/2002 | Wilson |
| 2002/0031125 A1 | 3/2002 | Sato |
| 2002/0054604 A1 | 5/2002 | Kadambi et al. |
| 2002/0069370 A1 | 6/2002 | Mack |
| 2002/0069375 A1 | 6/2002 | Bowen |
| 2002/0072893 A1 | 6/2002 | Wilson |
| 2002/0095512 A1 | 7/2002 | Rana et al. |
| 2002/0095519 A1 | 7/2002 | Philbrick et al. |
| 2002/0100029 A1 | 7/2002 | Bowen |
| 2002/0101425 A1 | 8/2002 | Hamid |
| 2002/0105911 A1 | 8/2002 | Pruthi et al. |
| 2002/0116508 A1 | 8/2002 | Khan et al. |
| 2002/0129140 A1 | 9/2002 | Peled et al. |
| 2002/0150248 A1 | 10/2002 | Kovacevic |
| 2002/0156998 A1 | 10/2002 | Casselman |
| 2002/0162025 A1 | 10/2002 | Sutton et al. |
| 2002/0166063 A1 | 11/2002 | Lachman et al. |
| 2002/0169873 A1 | 11/2002 | Zodnik |
| 2002/0180742 A1 | 12/2002 | Hamid |
| 2002/0199173 A1 | 12/2002 | Bowen |
| 2003/0009693 A1 | 1/2003 | Brock et al. |
| 2003/0014662 A1 | 1/2003 | Gupta et al. |
| 2003/0018630 A1 | 1/2003 | Indeck et al. |
| 2003/0023653 A1 | 1/2003 | Dunlop et al. |
| 2003/0023876 A1 | 1/2003 | Bardsley et al. |
| 2003/0028408 A1 | 2/2003 | RuDusky |
| 2003/0028690 A1 | 2/2003 | Appleby-Alis et al. |
| 2003/0028864 A1 | 2/2003 | Bowen |
| 2003/0033234 A1 | 2/2003 | RuDusky |
| 2003/0033450 A1 | 2/2003 | Appleby-Alis |
| 2003/0033514 A1 | 2/2003 | Appleby-Allis et al. |
| 2003/0033588 A1 | 2/2003 | Alexander |
| 2003/0033594 A1 | 2/2003 | Bowen |
| 2003/0035547 A1 | 2/2003 | Newton |
| 2003/0037037 A1 | 2/2003 | Adams et al. |
| 2003/0037321 A1 | 2/2003 | Bowen |
| 2003/0041129 A1 | 2/2003 | Appleby-Allis |
| 2003/0043805 A1 | 3/2003 | Graham et al. |
| 2003/0046668 A1 | 3/2003 | Bowen |
| 2003/0051043 A1 | 3/2003 | Wyschogrod et al. |
| 2003/0055658 A1 | 3/2003 | RuDusky |
| 2003/0055769 A1 | 3/2003 | RuDusky |
| 2003/0055770 A1 | 3/2003 | RuDusky |
| 2003/0055771 A1 | 3/2003 | RuDusky |
| 2003/0061409 A1 | 3/2003 | RuDusky |
| 2003/0065943 A1 | 4/2003 | Geis et al. |
| 2003/0074177 A1 | 4/2003 | Bowen |
| 2003/0074582 A1 | 4/2003 | Patel et al. |
| 2003/0079060 A1 | 4/2003 | Dunlop |
| 2003/0086300 A1 | 5/2003 | Noyes et al. |
| 2003/0105620 A1 | 6/2003 | Bowen |
| 2003/0110229 A1 | 6/2003 | Kulig et al. |
| 2003/0115485 A1 | 6/2003 | Milliken |
| 2003/0117971 A1 | 6/2003 | Aubury |
| 2003/0120460 A1 | 6/2003 | Aubury |
| 2003/0121010 A1 | 6/2003 | Aubury |
| 2003/0130899 A1 | 7/2003 | Ferguson et al. |
| 2003/0140337 A1 | 7/2003 | Aubury |
| 2003/0163715 A1 | 8/2003 | Wong |

(56) References Cited

U.S. PATENT DOCUMENTS

| | | |
|---|---|---|
| 2003/0177253 A1 | 9/2003 | Schuehler et al. |
| 2003/0184593 A1 | 10/2003 | Dunlop |
| 2003/0187662 A1 | 10/2003 | Wilson |
| 2003/0217306 A1 | 11/2003 | Harthcock et al. |
| 2003/0221013 A1 | 11/2003 | Lockwood et al. |
| 2004/0000928 A1 | 1/2004 | Cheng et al. |
| 2004/0010612 A1 | 1/2004 | Pandya |
| 2004/0015502 A1 | 1/2004 | Alexander et al. |
| 2004/0028047 A1 | 2/2004 | Hou et al. |
| 2004/0049596 A1 | 3/2004 | Schuehler et al. |
| 2004/0054924 A1 | 3/2004 | Chuah et al. |
| 2004/0062245 A1 | 4/2004 | Sharp et al. |
| 2004/0064737 A1 | 4/2004 | Milliken et al. |
| 2004/0073703 A1 | 4/2004 | Boucher et al. |
| 2004/0100977 A1 | 5/2004 | Suzuki et al. |
| 2004/0105458 A1 | 6/2004 | Ishizuka |
| 2004/0111632 A1 | 6/2004 | Halperin |
| 2004/0162826 A1 | 8/2004 | Wyschogrod et al. |
| 2004/0177340 A1 | 9/2004 | Hsu et al. |
| 2004/0205149 A1 | 10/2004 | Dillon et al. |
| 2005/0005145 A1 | 1/2005 | Teixeira |
| 2005/0044344 A1 | 2/2005 | Stevens |
| 2005/0086520 A1 | 4/2005 | Dharmapurikar et al. |
| 2005/0108518 A1 | 5/2005 | Pandya |
| 2005/0175010 A1 | 8/2005 | Wilson et al. |
| 2005/0187974 A1 | 8/2005 | Gong |
| 2005/0190787 A1 | 9/2005 | Kuik et al. |
| 2005/0195832 A1 | 9/2005 | Dharmapurikar et al. |
| 2005/0203938 A1 | 9/2005 | Hoeft et al. |
| 2005/0229254 A1 | 10/2005 | Singh et al. |
| 2005/0283743 A1 | 12/2005 | Mulholland et al. |
| 2006/0020715 A1 | 1/2006 | Jungck |
| 2006/0031263 A1 | 2/2006 | Arrouye et al. |
| 2006/0036693 A1 | 2/2006 | Hulten et al. |
| 2006/0047636 A1 | 3/2006 | Mohania et al. |
| 2006/0053295 A1 | 3/2006 | Madhusudan et al. |
| 2006/0075404 A1 | 4/2006 | Rosu et al. |
| 2006/0129745 A1 | 6/2006 | Thiel et al. |
| 2006/0146991 A1 | 7/2006 | Thompson et al. |
| 2006/0198375 A1 | 9/2006 | Baik et al. |
| 2006/0242123 A1 | 10/2006 | Williams, Jr. |
| 2006/0269148 A1 | 11/2006 | Farber et al. |
| 2006/0292292 A1 | 12/2006 | Brightman et al. |
| 2006/0294059 A1 | 12/2006 | Chamberlain et al. |
| 2007/0011183 A1 | 1/2007 | Langseth et al. |
| 2007/0011317 A1 | 1/2007 | Brandyburg et al. |
| 2007/0061594 A1 | 3/2007 | Ginter et al. |
| 2007/0067108 A1 | 3/2007 | Buhler et al. |
| 2007/0067481 A1 | 3/2007 | Sharma et al. |
| 2007/0078837 A1 | 4/2007 | Indeck et al. |
| 2007/0089063 A1 | 4/2007 | Breyer |
| 2007/0094199 A1 | 4/2007 | Deshpande et al. |
| 2007/0112837 A1 | 5/2007 | Houh et al. |
| 2007/0115986 A1 | 5/2007 | Shankara |
| 2007/0118494 A1 | 5/2007 | Jannarone et al. |
| 2007/0118500 A1 | 5/2007 | Indeck et al. |
| 2007/0130140 A1 | 6/2007 | Cytron et al. |
| 2007/0174841 A1 | 7/2007 | Chamberlain et al. |
| 2007/0179935 A1 | 8/2007 | Lee et al. |
| 2007/0209068 A1 | 9/2007 | Ansari et al. |
| 2007/0237327 A1 | 10/2007 | Taylor et al. |
| 2007/0260602 A1 | 11/2007 | Taylor |
| 2007/0277036 A1 | 11/2007 | Chamberlain et al. |
| 2007/0294157 A1 | 12/2007 | Singla et al. |
| 2008/0086274 A1 | 4/2008 | Chamberlain et al. |
| 2008/0109413 A1 | 5/2008 | Indeck et al. |
| 2008/0114724 A1 | 5/2008 | Indeck et al. |
| 2008/0114725 A1 | 5/2008 | Indeck et al. |
| 2008/0114760 A1 | 5/2008 | Indeck et al. |
| 2008/0126320 A1 | 5/2008 | Indeck et al. |
| 2008/0133453 A1 | 6/2008 | Indeck et al. |
| 2008/0133519 A1 | 6/2008 | Indeck et al. |
| 2008/0253395 A1 | 10/2008 | Pandya |
| 2009/0262741 A1 | 10/2009 | Jungck et al. |
| 2010/0174770 A1 | 7/2010 | Pandya |
| 2010/0198850 A1 | 8/2010 | Cytron et al. |
| 2011/0231446 A1 | 9/2011 | Buhler et al. |
| 2011/0252008 A1 | 10/2011 | Chamberlain et al. |
| 2011/0291615 A1 | 12/2011 | Pandya et al. |
| 2012/0109849 A1 | 5/2012 | Chamberlain et al. |
| 2012/0110316 A1 | 5/2012 | Chamberlain et al. |
| 2012/0116998 A1 | 5/2012 | Indeck et al. |
| 2012/0117610 A1 | 5/2012 | Pandya |
| 2012/0130922 A1 | 5/2012 | Indeck et al. |
| 2012/0215801 A1 | 8/2012 | Indeck et al. |
| 2013/0018835 A1 | 1/2013 | Pandya |
| 2013/0151458 A1 | 6/2013 | Indeck et al. |
| 2013/0159449 A1 | 6/2013 | Taylor et al. |
| 2013/0262287 A1 | 10/2013 | Parsons et al. |
| 2013/0290163 A1 | 10/2013 | Parsons et al. |
| 2014/0025656 A1 | 1/2014 | Indeck et al. |
| 2014/0040109 A1 | 2/2014 | Parsons et al. |
| 2014/0067830 A1 | 3/2014 | Buhler et al. |
| 2014/0089163 A1 | 3/2014 | Parsons et al. |
| 2014/0164215 A1 | 6/2014 | Parsons et al. |
| 2014/0180903 A1 | 6/2014 | Parsons et al. |
| 2014/0180904 A1 | 6/2014 | Parsons et al. |
| 2014/0180905 A1 | 6/2014 | Parsons et al. |
| 2014/0181133 A1 | 6/2014 | Parsons et al. |
| 2014/0310148 A1 | 10/2014 | Taylor et al. |
| 2014/0310717 A1 | 10/2014 | Chamberlain et al. |
| 2015/0023501 A1 | 1/2015 | Taylor et al. |
| 2015/0052148 A1 | 2/2015 | Indeck et al. |
| 2015/0055776 A1 | 2/2015 | Taylor et al. |
| 2016/0070583 A1 | 3/2016 | Chamberlain et al. |
| 2017/0102950 A1 | 4/2017 | Chamberlain et al. |
| 2017/0124255 A1 | 5/2017 | Buhler et al. |
| 2018/0157504 A1 | 6/2018 | Chamberlain et al. |
| 2018/0276271 A1 | 9/2018 | Parsons et al. |
| 2018/0330444 A1 | 11/2018 | Taylor et al. |
| 2019/0073719 A1 | 3/2019 | Parsons et al. |
| 2019/0155831 A1 | 5/2019 | Indeck et al. |
| 2019/0205975 A1 | 7/2019 | Taylor et al. |

FOREIGN PATENT DOCUMENTS

| | | |
|---|---|---|
| EP | 0887723 | 12/1998 |
| EP | 0989754 A2 | 3/2000 |
| JP | 57-137978 A | 8/1982 |
| JP | 58-102378 A | 6/1983 |
| JP | 61-107596 A | 5/1986 |
| JP | 63-143668 A | 6/1988 |
| JP | 03014075 | 1/1991 |
| JP | 04-205174 A | 7/1992 |
| JP | 05-101102 A | 4/1993 |
| JP | 05-217289 A | 8/1993 |
| JP | 09-054797 A | 2/1997 |
| JP | 9-269930 | 10/1997 |
| JP | 10313341 | 11/1998 |
| JP | 2000-076270 A | 3/2000 |
| JP | 2000285134 A | 10/2000 |
| JP | 2000286715 A | 10/2000 |
| JP | 2000357176 | 12/2000 |
| JP | 2001014239 | 1/2001 |
| JP | 2001217834 | 8/2001 |
| WO | 199409443 A1 | 4/1994 |
| WO | 1999055052 | 10/1999 |
| WO | 2000041136 A1 | 7/2000 |
| WO | 2001022425 A | 3/2001 |
| WO | 2001061913 | 8/2001 |
| WO | 2001080082 A2 | 10/2001 |
| WO | 2001080558 | 10/2001 |
| WO | 2002061525 | 8/2002 |
| WO | 2002082271 | 10/2002 |
| WO | 2003100650 | 4/2003 |
| WO | 2003036845 | 5/2003 |
| WO | 2003100662 | 12/2003 |
| WO | 2003104943 A2 | 12/2003 |
| WO | 2004014065 A2 | 2/2004 |
| WO | 2004017604 | 2/2004 |
| WO | 2004042560 A | 5/2004 |
| WO | 2004042561 A | 5/2004 |
| WO | 2004042562 | 5/2004 |
| WO | 2004042574 A | 5/2004 |

(56) References Cited

FOREIGN PATENT DOCUMENTS

| WO | 2005017708 A | 2/2005 |
|---|---|---|
| WO | 2005026925 | 3/2005 |
| WO | 2005048134 A | 5/2005 |
| WO | 2005081855 A2 | 9/2005 |
| WO | 2005114339 A2 | 12/2005 |
| WO | 2006023948 | 3/2006 |
| WO | 2006/059312 A2 | 6/2006 |
| WO | 2006060571 A2 | 6/2006 |
| WO | 2006096324 | 9/2006 |
| WO | 2007079095 A2 | 7/2007 |
| WO | 2008022036 | 2/2008 |
| WO | 2008073824 A1 | 6/2008 |

OTHER PUBLICATIONS

Dharmapurikar, "Fast and Scalable Pattern Matching for Content Filtering", ACM, ANCS 05, 2005, pp. 183-192.
Ebeling et al., "RaPiD—Reconfigurable Pipelined Datapath", University of Washington, Dept. of Computer Science and Engineering, Sep. 23, 1996, Seattle, WA.
Edgar, "MUSCLE: Multiple Sequence Alignment with High Accuracy and High Throughput", Nucleic Acids Research, 2004, vol. 32, No. 5, pp. 1792-1797.
Feldmann, "BLT: Bi-Layer Tracing of HTTP and TCP/IP", AT&T Labs—Research, Florham Park, NJ, USA, 2000.
Fernandez, "Template Matching of Binary Targets in Grey-Scale Images: A Nonparametric Approach", Pattern Recognition, 1997, pp. 1175-1182, vol. 30, No. 7.
Forgy, "RETE: A Fast Algorithm for the Many Pattern/Many Object Pattern Matching Problem", Artificial Intelligence, 1982, pp. 17-37, vol. 19.
Franklin et al., "An Architecture for Fast Processing of Large Unstructured Data Sets." Proc. of 22nd Int'l Conf. on Computer Design, Oct. 2004, pp. 280-287.
Franklin et al., "Assisting Network Intrusion Detection with Reconfigurable Hardware", Symposium on Field-Programmable Custom Computing Machines (FCCM 2002), Apr. 2002, Napa, California.
Fu et al., "The FPX KCPSM Module: An Embedded, Reconfigurable Active Processing Module for the Field Programmable Port Extender (FPX)", Washington University, Department of Computer Science, Technical Report WUCS-01-14, Jul. 2001.
Gaughan, "Data Streaming: Very Low Overhead Communication for Fine-Grained Multicomputing", 1995, <http://dx.doi.org/ 10.1109/SPDP.1995.530727>, 3 pages.
Gavrila et al., "Multi-feature Hierarchical Template Matching Using Distance Transforms", IEEE, Aug. 16-20, 1998, vol. 1, pp. 439-444.
Gokhale et al., "Reconfigurable Computing: Accelerating Computation With Field-Programmable Gate Arrays", 2005, pp. 1-3, 7, 11-15, 39, 92-93, Springer.
Gokhale et al., "Reconfigurable Computing: Accelerating Computation with Field-Programmable Gate Arrays", Springer, 2005, pp. 1-36.
Gokhale et al., "Reconfigurable Computing: Accelerating Computation with Field-Programmable Gate Arrays", Springer, 2005, pp. 1-54, 92-96.
Guerdoux-Jamet et al., "Systolic Filter for Fast DNA Similarity Search", IEEE, 1995, pp. 145-156.
Gunther et al., "Assessing Document Relevance with Run-Time Reconfigurable Machines", IEEE Symposium on FPGAs for Custom Computing Machines, 1996, pp. 10-17, Proceedings, Napa Valley, CA.
Gupta et al., "High-Speed Implementations of Rule-Based Systems," ACM Transactions on Computer Systems, May 1989, pp. 119-146, vol. 7, Issue 2.
Gupta et al., "Packet Classification on Multiple Fields", Computer Systems Laboratory, Stanford University, Stanford, CA, 2000.
Gupta et al., "PMM: A Parallel Architecture for Production Systems," Proceedings of the IEEE, Apr. 1992, pp. 693-696, vol. 2.

Gurtov, "Effect of Delays on TCP Performance", Cellular Systems Development, Sonera Corporation, online at http://cs.helsinki.fi/u/gurtov/papers/pwc01.pdf, 2000.
Gyang, "NCBI BLASTN Stage 1 in Reconfigurable Hardware," Technical Report WUCSE-2005-30, Aug. 2004, Department of Computer Science and Engineering, Washington University, St. Louis, MO.
Halaas et al., "A Recursive MISD Architecture for Pattern Matching", IEEE Transactions on Very Large Scale Integration, vol. 12, No. 7, pp. 727-734, Jul. 2004.
Hauck et al., "Software Technologies for Reconfigurable Systems", Northwestern University, Dept. of ECE, Technical Report, 1996.
Hayes, "Computer Architecture and Organization", Second Edition, 1988, pp. 448-459, McGraw-Hill, Inc.
Hezel et al., "FPGA-Based Template Matching Using Distance Transforms", Proceedings of the 10th Annual IEEE Symposium on Field-Programmable Custom Computing Machines, Apr. 22, 2002, pp. 89-97, IEEE Computer Society, USA.
Hollaar, "Hardware Systems for Text Information Retrieval", Proceedings of the Sixth Annual International ACM Sigir Conference on Research and Development in Information Retrieval, Jun. 6-8, 1983, pp. 3-9, Baltimore, Maryland, USA.
Hutchings et al., "Assisting Network Intrusion Detection with Reconfigurable Hardware", FCCM 2002: 10th Annual IEEE Symposium on Field-Programmable Custom Computing Machines, 2002.
Ibrahim et al., "Lecture Notes in Computer Science: Database and Expert Systems Applications", 2000, p. 769, vol. 1873, Springer.
International Search Report for PCT/US2001/011255 dated Jul. 10, 2003.
International Search Report for PCT/US2002/033286 dated Jan. 22, 2003.
International Search Report for PCT/US2003/015638 dated May 6, 2004.
International Search Report for PCT/US2004/016021 dated Aug. 18, 2005.
International Search Report for PCT/US2004/016398 dated Apr. 12, 2005.
International Search Report for PCT/US2005/030046; dated Sep. 25, 2006.
International Search Report for PCT/US2006/006105 dated Oct. 31, 2006.
International Search Report for PCT/US2007/060835 dated Jul. 9, 2007.
International Search Report for PCT/US2007/067319 dated Jan. 11, 2008.
International Search Report for PCT/US2007/075723 dated Jul. 25, 2008.
Invitation to Pay Additional Fees and Annex to Form PCT/ISA/206 Communication Relating to the Results of the Partial International Search for International Application PCT/US2003/015638 dated Feb. 3, 2004.
Jacobson et al., "RFC 1072: TCP Extensions for Long-Delay Paths", Oct. 1988.
Jacobson et al., "tcpdump—dump traffic on a network", Jun. 30, 1997, online at www.cse.cuhk.edu.hk/~cslui/CEG4430/tcpdump.ps.gz.
Jeanmougin et al., "Multiple Sequence Alignment with Clustal X", TIBS, 1998, vol. 23, pp. 403-405.
Johnson et al., "Pattern Matching in Reconfigurable Logic for Packet Classification", College of Computing, Georgia Institute of Technology, Atlanta, GA, 2000.
Jones et al., "A Probabilistic Model of Information Retrieval: Development and Status", Information Processing and Management, Aug. 1998, 76 pages.
Jung et al., "Efficient VLSI for Lempel-Ziv Compression in Wireless Data Communication Networks", IEEE Transactions on VLSI Systems, Sep. 1998, pp. 475-483, vol. 6, No. 3, Institute of Electrical and Electronics Engineers, Washington, DC, USA.
Keutzer et al., "A Survey of Programmable Platforms—Network Proc", University of California—Berkeley, pp. 1-29, 2000.

(56) References Cited

OTHER PUBLICATIONS

Koloniari et al., "Content-Based Routing of Path Queries in Peer-to-Peer Systems", pp. 1-19, E. Bertino et al. (Eds.): EDBT 2004, LNCS 2992, pp. 29-47, 2004, copyright by Springer-Verlag, Germany.
Krishnamurthy et al., "Biosequence Similarity Search on the Mercury System", Proceedings of the 15th IEEE International Conference on Application-Specific Systems, Architectures, and Processors (ASAP04), Sep. 2004, pp. 365-375.
Lancaster et al., "Acceleration of Ungapped Extension in Mercury BLAST", Seventh (7th) Workshop on Media and Streaming Processors, Nov. 12, 2005, Thirty-Eighth (38th) International Symposium on Microarchitecture (MICRO-38), Barcelona, Spain.
Roy, "A bounded search algorithm for segmented channel routing for FPGA's and associated channel architecture issues", IEEE, Nov. 11, 1993, pp. 1695-1705, vol. 12.
Russ et al., Non-Intrusive Built-In Self-Test for FPGA and MCM Applications, Aug. 8-10, 1995, IEEE, 480-485.
Schmit, "Incremental Reconfiguration for Pipelined Applications", FPGAs for Custom Computing Machines, Proceedings, The 5th Annual IEEE Symposium, Dept. of ECE, Carnegie Mellon University, Apr. 16-18, 1997, pp. 47-55, Pittsburgh, PA.
Schuehler et al., "Architecture for a Hardware Based, TCP/IP Content Scanning System", IEEE Micro, 24(1):62-69, Jan.-Feb. 2004, USA.
Schuehler et al., "TCP-Splitter: A TCP/IP Flow Monitor in Reconfigurable Hardware", Hot Interconnects 10 (Hotl-10), Stanford, CA, Aug. 21-23, 2002, pp. 127-131.
Seki et al., "High Speed Computation of Shogi With FPGA", Proceedings of 58th Convention Architecture, Software Science, Engineering, Mar. 9, 1999, pp. 1-133-1-134.
Shah, "Understanding Network Processors", Version 1.0, University of California—Berkeley, Sep. 4, 2001.
Shalunov et al., "Bulk TCP Use and Performance on Internet 2", ACM SIGCOMM Internet Measurement Workshop, 2001.
Shasha et al., "Database Tuning", 2003, pp. 280-284, Morgan Kaufmann Publishers, 2000.
Shirazi et al., "Quantitative Analysis of FPGA-based Database Searching", Journal of VLSI Signal Processing Systems for Signal, Image, and Video Technology, May 2001, pp. 85-96, vol. 28, No. 1/2, Kluwer Academic Publishers, Dordrecht, NL.
Sidhu et al., "Fast Regular Expression Matching Using FPGAs", IEEE Symposium on Field Programmable Custom Computing Machines (FCCM 2001), Apr. 2001.
Sidhu et al., "String Matching on Multicontext FPGAs Using Self-Reconfiguration", FPGA '99: Proceedings of the 1999 ACM/SIGDA 7th International Symposium on Field Programmable Gate Arrays, Feb. 1999, pp. 217-226.
Singh et al., "The EarlyBird System for Real-Time Detection on Unknown Worms", Technical report CS2003-0761, Aug. 2003.
Skiena et al., "Programming Challenges: The Programming Contest Training Manual", 2003, pp. 30-31, Springer.
Sourdis and Pnevmatikatos, "Fast, Large-Scale String Match for a 10Gbps FPGA-based Network Intrusion Detection System", 13th International Conference on Field Programmable Logic and Applications, 2003.
Srini, "DFS-SuperMPx: Low-Cost Parallel Processing System for Machine Vision and Image Processing", 1995, Retrieved from https://dialog.proquest.com/professional/docview/828015663?accountid=142257, 3 pages.
Steinbach et al., "A Comparison of Document Clustering Techniques", KDD Workshop on Text Mining, 2000.
Sugawara et al., "Over 10Gbps String Matching Mechanism for Multi-Stream Packet Scanning Systems", Field Programmable Logic and Application Lecture Notes in Computer Science, 2004, pp. 484-493, vol. 3203.
Tan et al., "A High Throughput String Matching Architecture for Intrusion Detection and Prevention", ISCA 2005: 32nd Annual International Symposium on Computer Architecture, pp. 112-122, 2005.
Tau et al., "A First Generation DPGA Implementation", Third Canadian Workshop of Field-Programmable Devices, May 1995, pp. 138-143.
Taylor et al., "Dynamic Hardware Plugins (DHP): Exploiting Reconfigurable Hardware for High-Performance Programmable Routers", Computer Networks, 38(3): 295-310 (16), Feb. 21, 2002, and online at http://www.cc.gatech.edu/classes/AY2007/cs8803hpc_fall/papers/phplugins.pdf.
Taylor et al., "Generalized RAD Module Interface Specification of the Field Programmable Port Extender (FPX) Version 2", Washington University, Department of Computer Science, Technical Report, Jul. 5, 2001, pp. 1-10.
Taylor et al., "Modular Design Techniques for the FPX", Field Programmable Port Extender: Jan. 2002 Gigabit Workshop Tutorial, Washington University, St. Louis, MO, Jan. 3-4, 2002.
Taylor et al., "Scalable Packet Classification using Distributed Crossproducting of Field Labels", Proceedings of IEEE Infocom, Mar. 2005, pp. 1-12, vol. 20, No. 1.
Taylor, "Models, Algorithms, and Architectures for Scalable Packet Classification", doctoral thesis, Department of Computer Science and Engineering, Washington University, St. Louis, MO, Aug. 2004, pp. 1-201.
Thompson et al., "The CLUSTAL_X Windows Interface: Flexible Strategies for Multiple Sequence Alignment Aided by Quality Analysis Tools", Nucleic Acids Research, 1997, vol. 25, No. 24, pp. 4876-4882.
Uluski et al., "Characterizing Antivirus Workload Execution", SIGARCH Comput. Archit. News, vol. 33, No. 1, pp. 90-98, Mar. 2005.
Villasenor et al., "Configurable Computing Solutions for Automatic Target Recognition", FPGAS for Custom Computing Machines, 1996, Proceedings, IEEE Symposium on Napa Valley, CA, Apr. 17-19, 1996, pp. 70-79, 1996 IEEE, Napa Valley, CA, Los Alamitos, CA, USA.
Waldvogel et al., "Scalable High-Speed Prefix Matching", ACM Transactions on Computer Systems, Nov. 2001, pp. 440-482, vol. 19, No. 4.
Ward et al., "Dynamically Reconfigurable Computing: A Novel Computation Technology with Potential to Improve National Security Capabilities", May 15, 2003, A White Paper Prepared by Star Bridge Systems, Inc. [retrieved Dec. 12, 2006]. Retrieved from the Internet: <URL: http://www.starbridgesystems.com/resources/whitepapers/Dynamically%20Reconfigurable%20Computing.pdf.
Weaver et al., "Very Fast Containment of Scanning Worms", Proc. USENIX Security Symposium 2004, San Diego, CA, Aug. 2004, located at http://www.icsi.berkely.edu/~nweaver/containment/containment.pdf.
West et al., "An FPGA-Based Search Engine for Unstructured Database", Proc. of 2nd Workshop on Application Specific Processors, Dec. 2003, San Diego, CA.
Wooster et al., "HTTPDUMP Network HTTP Packet Snooper", Apr. 25, 1996.
Xie et al., "A Scalable Bloom Filter for Membership Queries", IEEE, Nov. 2007, pp. 543-547.
Yamaguchi et al., "High Speed Homology Search with FPGAs", Proceedings Pacific Symposium on Biocomputing, Jan. 3-7, 2002, pp. 271-282, vol. 7, Online, Lihue, Hawaii, USA.
Yan et al., "Enhancing Collaborative Spam Detection with Bloom Filters", 2006, IEEE, pp. 414-425.
Yoshitani et al., "Performance Evaluation of Parallel Volume Rendering Machine Re Volver/C40", Study Report of Information Processing Society, Mar. 5, 1999, pp. 79-84, vol. 99, No. 21.
Ziv et al., "A Universal Algorithm for Sequential Data Compression", IEEE Trans. Inform. Theory, IT-23(3): 337-343 (1997).
Ziv et al., "Compression of Individual Sequence via Variable-Rate Coding", IEEE Transactions on Information Theory, Sep. 1978, pp. 530-536, vol. IT-24, No. 5, Institute of Electrical and Electronics Engineers, Washington, DC, USA.
"A Reconfigurable Computing Model for Biological Research Application of Smith-Waterman Analysis to Bacterial Genomes" A White Paper Prepared by Star Bridge Systems, Inc. [retrieved Dec. 12,

(56) References Cited

OTHER PUBLICATIONS

2006]. Retrieved from the Internet: <URL: http://www.starbridgesystems.com/resources/whitepapers/Smith%20Waterman%20Whitepaper.pdf.

"Lucent Technologies Delivers "PayloadPlus" Network Processors for Programmable, MultiProtocol, OC-48c Processing", Lucent Technologies Press Release, downloaded from http://www.lucent.com/press/1000/0010320.meb.html on Mar. 21, 2002.

"Overview, Field Programmable Port Extender", Jan. 2002 Gigabit Workshop Tutorial, Washington University, St. Louis, MO, Jan. 3-4, 2002, pp. 1-4.

"Payload Plus™ Agere System Interface", Agere Systems Product Brief, Jun. 2001, downloaded from Internet, Jan. 2002, pp. 1-6.

"RFC793: Transmission Control Protocol, Darpa Internet Program, Protocol Specification", Sep. 1981.

"Technology Overview", Data Search Systems Incorporated, downloaded from the http://www.datasearchsystems.com/tech.htm on Apr. 19, 2004.

"The Field-Programmable Port Extender (FPX)", downloaded from http://www.arl.wustl.edu/arl/ in Mar. 2002.

Aldwairi et al., "Configurable String Matching Hardware for Speeding up Intrusion Detection", SIRARCH Comput. Archit. News, vol. 33, No. 1, pp. 99-107, Mar. 2005.

Altschul et al., "Basic Local Alignment Search Tool", J. Mol. Biol., Oct. 5, 1990, 215, pp. 403-410.

Amanuma et al., "A FPGA Architecture for High Speed Computation", Proceedings of 60th Convention Architecture, Software Science, Engineering, Mar. 14, 2000, pp. 1-163-1-164, Information Processing Society, Japan.

Amer-Yahia et al., "XQuery 1.0 and XPath 2.0 Full-Text 1.0", W3C Working Draft, http://www.w3.org/TR/query-full-text/, May 18, 2007—parts 1-4.

Anerousis et al., "Using the AT&T Labs PacketScope for Internet Measurement, Design, and Performance Analysis", Network and Distributed Systems Research Laboratory, AT&T Labs—Research, Florham, Park, NJ, Oct. 1997.

Arnold et al., "The Splash 2 Processor and Applications", Proceedings 1993 IEEE International Conference on Computer Design: VLSI in Computers and Processors (ICCD '93), Oct. 3, 1993, pp. 482-485, IEEE Computer Society, Cambridge, MA USA.

Artan et al., "Multi-packet Signature Detection using Prefix Bloom Filters", 2005, IEEE, pp. 1811-1816.

Asami et al., "Improvement of DES Key Search on FPGA-Based Parallel Machine "RASH"", Proceedings of Information Processing Society, Aug. 15, 2000, pp. 50-57, vol. 41, No. SIG5 (HPS1), Japan.

Baboescu et al., "Scalable Packet Classification," SIGCOMM'01, Aug. 27-31, 2001, pp. 199-210, San Diego, California, USA; http://www.ecse.rpi.edu/homepages/shivkuma/teaching/sp2001/readings/baboescu-pkt-classification.pdf.

Baer, "Computer Systems Architecture", 1980, pp. 262-265; Computer Science Press, Potomac, Maryland.

Baeza-Yates et al., "New and Faster Filters for Multiple Approximate String Matching", Random Structures and Algorithms (RSA), Jan. 2002, pp. 23-49, vol. 20, No. 1.

Baker et al., "High-throughput Linked-Pattern Matching for Intrusion Detection Systems", ANCS 2005: Proceedings of the 2005 Symposium on Architecture for Networking and Communications Systems, pp. 193-202, ACM Press, 2005.

Baker et al., "Time and Area Efficient Pattern Matching on FPGAs", ACM, Feb. 22-24, 2004, pp. 223-232.

Behrens et al., "BLASTN Redundancy Filter in Reprogrammable Hardware," Final Project Submission, Fall 2003, Department of Computer Science and Engineering, Washington University.

Berk, "JLex: A lexical analyzer generator for Java™", downloaded from http://www.cs.princeton.edu/~appel/modern/java/JLex/ in Jan. 2002, pp. 1-18.

Bloom, "Space/Time Trade-offs in Hash Coding With Allowable Errors", Communications of the ACM, Jul. 1970, pp. 422-426, vol. 13, No. 7, Computer Usage Company, Newton Upper Falls, Massachusetts, USA.

Braun et al., "Layered Protocol Wrappers for Internet Packet Processing in Reconfigurable Hardware", Proceedings of Hot Interconnects 9 (Hotl-9) Stanford, CA, Aug. 22-24, 2001, pp. 93-98.

Braun et al., "Protocol Wrappers for Layered Network Packet Processing in Reconfigurable Hardware", IEEE Micro, Jan.-Feb. 2002, pp. 66-74.

Cavnar et al., "N-Gram-Based Text Categorization", Proceedings of SDAIR-94, 3rd Annual Symposium on Document Analysis and Information Retrieval, Las Vegas, pp. 161-175, 1994.

Celko, "Joe Celko's Data & Databases: Concepts in Practice", 1999, pp. 72-74, Morgan Kaufmann Publishers.

Chamberlain et al., "Achieving Real Data Throughput for an FPGA Co-Processor on Commodity Server Platforms", Proc. of 1st Workshop on Building Block Engine Architectures for Computers and Networks, Oct. 2004, Boston, MA.

Chamberlain et al., "The Mercury System: Embedding Computation Into Disk Drives", 7th High Performance Embedded Computing Workshop, Sep. 2003, Boston, MA.

Chamberlain et al., "The Mercury System: Exploiting Truly Fast Hardware for Data Search", Proc. of Workshop on Storage Network Architecture and Parallel I/Os, Sep. 2003, New Orleans, LA.

Chaney et al., "Design of a Gigabit ATM Switch", Washington University, St. Louis, 2000.

Chenna et al., "Multiple Sequence Alignment with the Clustal Series of Programs", Nucleic Acids Research, 2003, vol. 31, No. 13, pp. 3497-3500.

Cho et al., "Deep Packet Filter with Dedicated Logic and Read Only Memories", 12th Annual IEEE Symposium on Field-Programmable Custom Computing Machines, Apr. 2004.

Chodowiec et al., "Fast Implementations of Secret-Key Block Ciphers Using Mixed Inter- and Outer-Round Pipelining", Proceedings of International Symposium on FPGAs, pp. 94-102 (Feb. 2001).

Choi et al., "Design of a Flexible Open Platform for High Performance Active Networks", Allerton Conference, 1999, Champaign, IL.

Chuanxiong et al., "Analysis and Evaluation of the TCP/IP Protocol Stack of LINUX*", 2000 International Conference on Communication Technology Proceedings, Aug. 21-25, 2000, pp. 444-453, vol. 1, Beijing, China.

Clark et al., "Scalable Pattern Matching for High Speed Networks", Proceedings of the 12th Annual IEEE Symposium on Field-Programmable Custom Computing Machines, 2004; FCCM 2004, Apr. 20-23, 2004; pp. 249-257; IEEE Computer Society; Cambridge, MA USA.

Cloutier et al., "VIP: An FPGA-Based Processor for Image Processing and Neural Networks", Proceedings of Fifth International Conference on Microelectronics for Neural Networks, Feb. 12, 1996, pp. 330-336, Los Alamitos, California.

Compton et al., "Configurable Computing: A Survey of Systems and Software", Technical Report, Northwestern University, Dept. of ECE, 1999.

Compton et al., "Reconfigurable Computing: A Survey of Systems and Software", Technical Report, Northwestern University, Dept. of ECE, 1999, presented by Yi-Gang Tai.

Compton et al., "Reconfigurable Computing: A Survey of Systems and Software", University of Washington, ACM Computing Surveys, Jun. 2, 2002, pp. 171-210, vol. 34 No. 2, <http://www.idi.ntnu.no/emner/tdt22/2011/reconfig.pdf>.

Cong et al., "An Optional Technology Mapping Algorithm for Delay Optimization in Lookup-Table Based FPGA Designs", IEEE, 1992, pp. 48-53.

Cuppu and Jacob, "Organizational Design Trade-Offs at the DRAM, Memory Bus and Memory Controller Level: Initial Results," Technical Report UMB-SCA-1999-2, Univ. of Maryland Systems & Computer Architecture Group, Nov. 1999, pp. 1-10.

Currid, "TCP Offload to the Rescue", Networks, Jun. 14, 2004, 16 pages, vol. 2, No. 3.

Dehon, "DPGA-coupled Microprocessors Commodity ICs for the Early 21st Century", Institute of Electrical and Electronics Engineers, 1994, pp. 31-39.

(56) References Cited

OTHER PUBLICATIONS

Denoyer et al., "HMM-based Passage Models for Document Classification and Ranking", Proceedings of ECIR-01, 23rd European Colloquim Information Retrieval Research, Darmstatd, DE, pp. 126-135, 2001.
Dharmapurikar et al., "Deep Packet Inspection Using Parallel Bloom Filters," IEEE Micro, Jan.-Feb. 2004, vol. 24, Issue: 1, pp. 52-61.
Dharmapurikar et al., "Deep Packet Inspection Using Parallel Bloom Filters," Symposium on High Performance Interconnects (Hotl), Stanford, California, 2003, pp. 44-51.
Dharmapurikar et al., "Design and Implementation of a String Matching System for Network Intrusion Detection using FPGA-based Bloom Filters", Proc. of 12th Annual IEEE Symposium on Field Programmable Custom Computing Machines, 2004, pp. 1-10.
Dharmapurikar et al., "Longest Prefix Matching Using Bloom Filters," SIGCOMM, 2003, pp. 201-212.
Li et al., "Large-Scale IP Traceback in High-Speed Internet: Practical Techniques and Theoretical Foundation", Proceedings of the 2004 IEEE Symposium on Security and Privacy, 2004, pp. 1-15.
Lin et al., "Real-Time Image Template Matching Based on Systolic Array Processor", International Journal of Electronics; Dec. 1, 1992; pp. 1165-1176; vol. 73, No. 6; London, Great Britain.
Lockwood et al., "Field Programmable Port Extender (FPX) for Distributed Routing and Queuing", ACM International Symposium on Field Programmable Gate Arrays (FPGA 2000), Monterey, CA, Feb. 2000, pp. 137-144.
Lockwood et al., "Hello, World: A Simple Application for the Field Programmable Port Extender (FPX)", Washington University, Department of Computer Science, Technical Report WUCS-00-12, Jul. 11, 2000.
Lockwood et al., "Parallel FPGA Programming over Backplane Chassis", Washington University, Department of Computer Science, Technical Report WUCS-00-11, Jun. 12, 2000.
Lockwood et al., "Reprogrammable Network Packet Processing on the Field Programmable Port Extender (FPX)", ACM International Symposium on Field Programmable Gate Arrays (FPGA 2001), Monterey, CA, Feb. 2001, pp. 87-93.
Lockwood, "An Open Platform for Development of Network Processing Modules in Reprogrammable Hardware", IEC DesignCon 2001, Santa Clara, CA, Jan. 2001, Paper WB-19.
Lockwood, "Building Networks with Reprogrammable Hardware", Field Programmable Port Extender: Jan. 2002 Gigabit Workshop Tutorial, Washington University, St. Louis, MO, Jan. 3-4, 2002.
Lockwood, "Evolvable Internet Hardware Platforms", NASA/DoD Workshop on Evolvable Hardware (EHW'01), Long Beach, CA, Jul. 12-14, 2001, pp. 271-279.
Lockwood, "Hardware Laboratory Configuration", Field Programmable Port Extender: Jan. 2002 Gigabit Workshop Tutorial, Washington University, St. Louis, MO, Jan. 3-4, 2002.
Lockwood, "Introduction", Field Programmable Port Extender: Jan. 2002 Gigabit Workshop Tutorial, Washington University, St. Louis, MO, Jan. 3-4, 2002.
Lockwood, "Platform and Methodology for Teaching Design of Hardware Modules in Internet Routers and Firewalls", IEEE Computer Society International Conference on Microelectronic Systems Education (MSE'2001), Las Vegas, NV, Jun. 17-18, 2001, pp. 56-57.
Lockwood, "Protocol Processing on the FPX", Field Programmable Port Extender: Jan. 2002 Gigabit Workshop Tutorial, Washington University, St. Louis, MO, Jan. 3-4, 2002.
Lockwood, "Simulation and Synthesis", Field Programmable Port Extender: Jan. 2002 Gigabit Workshop Tutorial, Washington University, St. Louis, MO, Jan. 3-4, 2002.
Lockwood, "Simulation of the Hello World Application for the Field-Programmable Port Extender (FPX)", Washington University, Applied Research Lab, Spring 2001 Gigabits Kits Workshop.
Madhusudan, "Design of a System for Real-Time Worm Detection", Hot Interconnects, pp. 77-83, Stanford, CA, Aug. 2004, found at http://www.hoti.org/hoti12/program/papers/2004/paper4.2.pdf.
Madhusudan, "Design of a System for Real-Time Worm Detection", Power Point Presentation in Support of Master's Thesis, Washington Univ., Dept. of Computer Science and Engineering, St. Louis, MO, Aug. 2004.
Mao et al., "Cluster-based Online Monitoring System of Web Traffic", Dept. of Computer Science and Technology, Tsinghua Univ., Bejing, 100084 P.R. China, 2000.
Mitzenmacher, "Compressed Bloom Filters", IEEE/ACM Transactions on Networking, Oct. 2002 (manuscript revised Dec. 5, 2001), pp. 604-612, vol. 10, No. 5, U.S.A.
Mosanya et al., "A FPGA-Based Hardware Implementation of Generalized Profile Search Using Online Arithmetic", ACM/Sigda International Symposium on Field Programmable Gate Arrays (FPGA '99), Feb. 21-23, 1999, pp. 101-111, Monterey, CA, USA.
Moscola et al., "FPGrep and FPSed: Regular Expression Search and Substitution for Packet Streaming in Field Programmable Hardware", Dept. of Computer Science, Applied Research Lab, Washington University, Jan. 8, 2002, unpublished, pp. 1-19, St. Louis, MO.
Moscola et al., "FPSed: A Streaming Content Search-and-Replace Module for an Internet Firewall", Proc. of Hot Interconnects, 11th Symposium on High Performance Interconnects, pp. 122-129, Aug. 20, 2003.
Moscola, "FPGrep and FPSed: Packet Payload Processors for Managing the Flow of Digital Content on Local Area Networks and the Internet", Master's Thesis, Sever Institute of Technology, Washington University, St. Louis, MO, Aug. 2003.
Motwani et al., "Randomized Algorithms", 1995, pp. 215-216, Cambridge University Press.
Navarro, "A Guided Tour to Approximate String Matching", ACM Computing Surveys, vol. 33, No. 1, Mar. 2001, pp. 31-88.
Necker et al., "TCP-Stream Reassembly and State Tracking in Hardware", School of Electrical and Computer Engineering, Georgia Institute of Technology, Atlanta, GA, 2000.
Niewczas et al., "A Pattern Matching Algorithm for Verification and Analysis of Very Large IC Layouts", ACM, Apr. 1998, pp. 129-134.
Nunez et al., "The X-MatchLITE FPGA-Based Data Compressor", Euromicro Conference 1999, Proceedings, Italy, Sep. 8-10, 1999, pp. 126-132, Los Alamitos, CA.
Nwodoh et al., "A Processing System for Real-Time Holographic Video Computation", Reconfigurable Technology: FPGAs for Computing and Application, Proceedings for the SPIE, Sep. 1999, Boston, pp. 129-140, vol. 3844.
Office Action for U.S. Appl. No. 11/381,214 dated Feb. 11, 2009.
Office Action for U.S. Appl. No. 11/381,214 dated Jun. 26, 2008.
Office Action for U.S. Appl. No. 11/836,947 dated Feb. 5, 2009.
Office Action for U.S. Appl. No. 11/836,947 dated Oct. 19, 2009.
Office Action for U.S. Appl. No. 11/932,321 dated Apr. 30, 2009.
Partial International Search Report for PCT/US03/15638 dated Feb. 3, 2004.
Pirsch et al., "VLSI Architectures for Video Compression—A Survey", Proceedings of the IEEE, Feb. 1995, pp. 220-243, vol. 83, No. 2, Institute of Electrical and Electronics Engineers, Washington, DC, USA.
Prakash et al., "OC-3072 Packet Classification Using BDDs and Pipelined SRAMs", Department of Electrical and Computer Engineering, The University of Texas at Austin, 2000.
Pramanik et al., "A Hardware Pattern Matching Algorithm on a Dataflow"; Computer Journal; Jul. 1, 1985; pp. 264-269; vol. 28, No. 3; Oxford University Press, Surrey, Great Britain.
Prosecution History for U.S. Appl. No. 13/969,935, U.S. Pat. No. 9,547,680, filed Aug. 19, 2013.
Prosecution History for U.S. Appl. No. 11/359,285, filed Feb. 22, 2006 (Buhler et al.).
Prosecution History for U.S. Appl. No. 13/046,395, now U.S. Pat. No. 8,515,682, filed Mar. 11, 2011 (Buhler et al.).
Ramakrishna et al., "A Performance Study of Hashing Functions for Hardware Applications", Int. Conf. on Computing and Information, May 1994, pp. 1621-1636, vol. 1, No. 1.
Ramakrishna et al., "Efficient Hardware Hashing Functions for High Performance Computers", IEEE Transactions on Computers, Dec. 1997, vol. 46, No. 12.

(56) References Cited

OTHER PUBLICATIONS

Ramakrishna et al., "Perfect Hashing Functions for Hardware Applications", IEEE, Apr. 1991, pp. 464-470.

Ramesh et al., "Automatic Selection of Tuning Parameters for Feature Extraction Sequences", IEEE, Jun. 21-23, 1994, pp. 672-677.

Ranganathan et al., "High-Speed VLSI Designs for Lempe-Ziv Based Data Compression", IEEE Transactions on Circuits and Systems—II: Analog and Digital Signal Processing, Feb. 1993, pp. 96-106, vol. 40, No. 2, Institute of Electrical and Electronics Engineers, Washington, DC, USA.

Ratha et al., "Convolution on Splash 2", Proceedings of IEEE Symposium on FPGAS for Custom Computing Machines, Apr. 19, 1995, pp. 204-213, Los Alamitos, California.

Ratha et al., "FPGA-based coprocessor for text string extraction", IEEE, Sep. 11-13, 2000, pp. 217-221.

Roberts, "Internet Still Growing Dramatically Says Internet Founder", Press Release, Caspian Networks, Inc.—Virtual Pressroom, 2000.

Roesch, "Snort—Lightweight Intrusion Detection for Networks", Proceedings of LISA '99: 13th Systems Administration Conference; Nov. 7-12, 1999; pp. 229-238; USENIX Association, Seattle, WA USA.

Prosecution History for U.S. Appl. No. 15/403,687, filed Jan. 11, 2017, now U.S. Pat. No. 10,580,518.

OrCAD unveils strategy for leadership of mainstream programmable logic design market; strategy includes partnerships and a next generation product, OrCAD express for windows: A shrink-wrapped 32-bit windows application that includes VHDL simulation and synthesis. (Jun. 3, 1996). Retrieved Sep. 16, 2020 (Year: 1996).

Smith, E. (Oct. 10, 1994). QuickLogic QuickWorks guarantees fastest FPGA design cycle. Business Wire Retrieved from https://dialog.proquest.com/professional/docview/447031280?accountid=131444 <https://dialog.proquest.com/professional/docview/447031280?accountid=131444> retrieved Sep. 16, 2020 (Year: 1994).

\* cited by examiner

Sample biosequence data stream 120

Sample w-mers produced by Input Processing Unit 104 from stream 120 and to the Bloom Filter Stage 106 (where w=11 and where q=8)

NCBI BLAST

```
         |←—————————————— 62 ——————————————→|
         |←——————————————5-mer——|————————————→|
Query    |A T C C T G A T C G A T C G G T A C A G A T|C T T G C A A A G T C A A G T G T C|
Subject  |C A G T G A T A C G A T G T G A A C A G A T|C A T G C A T T T C A C A G C A T A|
Comparison Score -3 -3  1 1 1 1 -3 -3 1 -3 1 1 1  1 1 1 | 1 -3 1 1 1 1 -3 -3 -3 -3
Running Score    -4 -1  2 1 0 -1 -2 1 4 3 6 5 4  3 2 1 | 1 -2 -1 0 1 2 -1 -4 -7 -10
X-drop = 10
                                          |————————— maximal scoring substring
                                                       (score = 8)
```

PRIOR ART

Figure 9

```
1   Extension (w-mer)
2     Calculate window boundaries
3     Γ = γ = 0
4     B = Bmax = Emax = 0
5
6     for i = 1...Lw
7       if qi = si
8         γ = γ + α
9       else
10        γ = γ - β
11
12      if γ > 0
13        if γ > Γ and i > WmerEnd
14          Γ = γ
15          Bmax = B
16          Emax = i
17      else if i < WmerStart
18        B = i + 1
19        γ = 0
20
21    if Γ > T or Bmax = 0 or Emax = Lw
22        return True
23    else
24        return False
```

METHOD AND APPARATUS FOR PERFORMING SIMILARITY SEARCHING

CROSS-REFERENCE AND PRIORITY CLAIM TO RELATED APPLICATIONS

This application is a continuation of U.S. patent application Ser. No. 15/403,687 filed Jan. 11, 2017, now U.S. Pat. No. 10,580,518, which is a divisional of U.S. patent application Ser. No. 13/969,935 filed Aug. 19, 2013, now U.S. Pat. No. 9,547,680, which is a divisional of U.S. patent application Ser. No. 13/046,395, filed Mar. 11, 2011, now U.S. Pat. No. 8,515,682, which is a divisional of U.S. patent application Ser. No. 11/359,285, filed Feb. 22, 2006, now U.S. Pat. No. 7,917,299, the entire disclosures of which are incorporated herein by reference, which claims the benefit of U.S. Provisional Application No. 60/658,418, filed on Mar. 3, 2005 and also claims the benefit of U.S. Provisional Application No. 60/736,081, filed on Nov. 11, 2005.

STATEMENT REGARDING FEDERALLY SPONSORED RESEARCH OR DEVELOPMENT

This invention was made with government support under 0217334, 0237902, 0313203, and 0427794 awarded by the National Science Foundation and HG003225 awarded by the National Institutes of Health (NIH). The government has certain rights in the invention.

THE NAMES OF PARTIES TO A JOINT RESEARCH AGREEMENT

Washington University, a corporation of the State of Missouri, and Data Search Systems, Inc., a corporation of the State of Delaware (now Exegy Incorporated, a corporation of the State of Delaware), are parties to a Joint Research Agreement.

FIELD OF THE INVENTION

The present invention relates to the field of biosequence similarity searching. In particular, the present invention relates to the field of searching large databases of biological sequences for strings that match a query sequence.

BACKGROUND OF THE INVENTION

The amount of biosequence data being produced each year is growing exponentially. Extracting useful information from this massive amount of data efficiently is becoming an increasingly difficult task. The databases of genomic DNA and protein sequences are an essential resource for modern molecular biology. This is where a computational search of these databases can show that a DNA sequence acquired in the lab is similar to other sequences of a known biological function, revealing both its role in the cell and its history over evolutionary time. A decade of improvement in DNA sequencing technology has driven exponential growth of biosequence databases such as NCBI GenBank, which has doubled in size every twelve (12) to sixteen (16) months for the last decade and now stands at over forty-five (45) billion characters. These technological gains have also generated more novel sequences, including entire mammalian genomes, which keep search engines very busy.

Examples of this type of searching can be found in a paper entitled *Biosequence Similarity Search On The Mercury System*, P. Krishnamurthy, J. Buhler, R. D. Chamberlain, M. A. Franklin, K. Gyang, and J. Lancaster, In Proceedings of the 15th IEEE International Conference on Application-Specific Systems, Architectures, and Processors (ASAP04), September 2004, Pages 365-375 (2004). Another example is a paper entitled: *NCBI BLASTN STAGE* 1 *IN RECONFIGURABLE HARDWARE*, by Kwame Gyang, Department of Computer Science and Engineering, Washington University, August 2004, Technical Report WUCSE-2005-30. Another example is a paper entitled "*BLASTN Redundancy Filter in Reprogrammable Hardware*", by C. Behrens, J. Lancaster, and B. Wun, Department of Computer Science and Engineering, Washington University, Final Project Submission, Fall 2003. These papers are each incorporated by reference, in their entirety.

There is a growing need for a fast and cost effective mechanism for extracting useful information from biosequence data.

SUMMARY OF INVENTION

In one aspect of this invention, an apparatus is disclosed for comparing a first biosequence string with a second biosequence string to assess similarity between the first and second biosequence strings, the apparatus comprising a field programmable gate array (FPGA), the FPGA configured to (1) detect substrings of the second biosequence string that are matches to substrings of the first biosequence string, and (2) map the detected substrings of the second biosequence string to corresponding positions in the first biosequence string where the detected substrings are located based on a data structure that links substrings of the first biosequence string to positions in the first biosequence string where the substrings of the first biosequence string are located.

In another aspect of this invention, an apparatus is disclosed for comparing a first biosequence string with a second biosequence string to assess similarity between the first and second biosequence strings, the apparatus comprising a field programmable gate array (FPGA), the FPGA configured to process a stream of the second biosequence string through a pipeline resident on the FPGA, wherein the pipeline is configured to (1) map positions within the first and second biosequence strings to each other based where matches exist within the first and second biosequence strings between substrings of the first and second biosequence strings, and (2) based on the mapped positions of the first and second biosequence strings, find an alignment between longer substrings of the first and second biosequence substrings for which a similarity between the aligned longer substrings is above a threshold.

In another aspect of this invention, an apparatus is disclosed for comparing a first biosequence string with a second biosequence string to assess similarity between the first and second biosequence strings, the apparatus comprising a field programmable gate array (FPGA), wherein the FPGA is configured to (1) detect a substring of the second biosequence string that matches a substring of the first biosequence string, (2) map the detected substring of the second biosequence string to a position in the first biosequence string where the detected substring is located, (3) perform a comparison between a longer substring of the second biosequence string and a corresponding longer substring of the first biosequence substring, wherein the longer substring of the second biosequence string encompasses the detected and mapped substring, and wherein the corresponding longer substring of the first biosequence string encompasses the mapped position for the detected and mapped substring, (4) quantify a similarity between the longer substrings of the first and second biosequence strings based on the comparison, and (5) perform the detect, map, comparison, and quantify operations with respect to a plurality of different substrings of the first and second biosequence strings.

In still another aspect of this invention, a method is disclosed for comparing a first biosequence string with a second biosequence string to assess similarity between the first and second biosequence strings, the method comprising (1) a field programmable gate array (FPGA) comparing a first substring of the first biosequence string with a first substring of the second biosequence string to quantify a similarity between the first substring of the first biosequence string and the first substring of the second biosequence string, (2) the FPGA seeding the comparing step by detecting a position within the first biosequence substring and a position within the second biosequence substring which correspond to second substrings of the first and second biosequence strings respectively that match each other, wherein the first substrings are longer than the second substrings, and (3) the FPGA performing the seeding and comparing steps with respect to a plurality of different substrings of the first and second biosequence strings.

In still aspect of this invention, a digital logic circuit for performing biological sequence similarity searching is disclosed. This digital logic circuit includes a programmable logic device configured to include a pipeline comprising a Bloom filter stage, the Bloom filter stage being configured to receive a data stream comprising a plurality of biological sequence data strings and filter the biological sequence data stream to identify a plurality of possible matches between the sequence data strings and a plurality of substrings of a query string.

In yet another aspect of this invention, a system for performing seeded alignment searching is disclosed. This system includes reconfigurable hardware configured to implement a seeded alignment searching pipeline, the pipeline comprising a Bloom filter stage, the Bloom filter stage being configured to receive a data stream, the data stream comprising a plurality of data strings and filter the data stream to identify a plurality of possible matches between the stream data strings and a plurality of substrings of a query string.

In still another aspect of this invention, a method for performing biological sequence similarity searching is disclosed. This method includes processing a biological sequence data stream through a Bloom filter stage implemented on a programmable logic device, the biological sequence data stream comprising a plurality of biological sequence data strings, the Bloom filter stage comprising a Bloom filter that is programmed with a plurality of sub strings of a query string and configured to identify a plurality of possible matches between the biological sequence data strings and the query substrings.

In yet another aspect of this invention, a digital logic circuit for performing biological sequence similarity searching is disclosed. This digital logic circuit includes a programmable logic device configured to include a pipeline that comprises a matching stage, the matching stage being configured to receive a data stream comprising a plurality of possible matches between a plurality of biological sequence data strings and a plurality of substrings of a query string and the pipeline further comprises a prefilter stage located downstream from the matching stage, the prefilter stage being configured to shift through pattern matches between the biological sequence data strings and the plurality of substrings of a query string and provide a score so that only pattern matches that exceed a user defined score will pass downstream from the prefilter stage.

In still yet another aspect of this invention, a method for performing biological sequence similarity searching is disclosed. This method includes processing a biological sequence data stream with a programmable logic device configured to include a pipeline that comprises a matching stage, the matching stage being configured to receive a data stream comprising a plurality of possible matches between a plurality of biological sequence data strings and a plurality of substrings of a query string and utilizing a prefilter stage located downstream from the matching stage in the pipeline, the prefilter stage being configured to shift through pattern matches between the biological sequence data strings and the plurality of substrings of a query string and provide a score so that only pattern matches that exceed a user defined score pass will downstream from the prefilter stage.

These are merely some of the innumerable aspects of the present invention and should not be deemed an all-inclusive listing of the innumerable aspects associated with the present invention.

BRIEF DESCRIPTION OF DRAWINGS

For a better understanding of the present invention, reference may be made to the accompanying drawings in which:

FIG. 4 depicts a sample portion of a biological sequence data stream;

FIG. 5 depicts a query sequence can be broken down into multiple w-mers in connection with the database sequence shown in FIG. 3;

FIG. 9 depicts an exemplary data window associated with the analysis of ungapped extension with analysis in two directions within a predefined window of data;

DETAILED DESCRIPTION OF THE INVENTION

Figure 1:
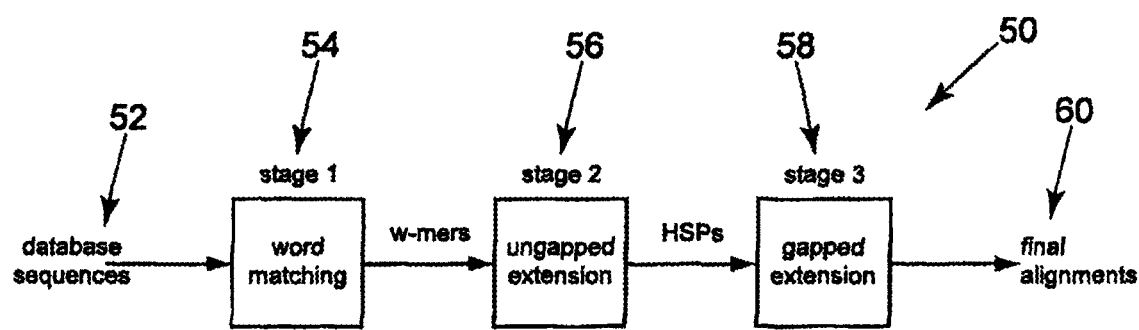
FIG. 1 provides a block diagram overview of a three (3) stage pipeline in accordance with a preferred, nonlimiting, illustrative embodiment of the present invention broken down into three (3) main stages.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to obscure the present invention.

In an effort to improve upon the speed of biological similarity searching, the inventors herein have developed a novel and unique method and system whereby Stage 1 of the software pipeline known in the art as BLAST (Basic Local Alignment Search Tool), and more particularly the BLAST application BLASTN, is implemented via programmable logic device, e.g., reconfigurable hardware, such as, but not limited to, FPGAs (field programmable gate arrays). In addition, this present invention decides in Stage 2 of the software pipeline, ungapped extension, whether each w-mer emitted from word matching is worth inspecting by the more computationally intensive, gapped extension by shifting through pattern matches between query and database. It is important to identify and discard spurious w-mers as early as possible in the BLAST pipeline because later stages are increasingly more complex.

BLAST compares a query sequence to a biosequence database to find other sequences that differ from it by a small number of edits (single-character insertions, deletions, or substitutions). Because direct measurement of the edit distance between sequences is computationally expensive, BLAST uses a variety of heuristics to identify small portions of a large database that are worth comparing carefully to the biosequence query.

BLAST includes a pipeline of computations that filter a stream of characters from a database to identify meaningful matches to a query. To keep pace with growing databases and queries, this stream must be filtered at increasingly higher rates. One path to higher performance is to develop a specialized processor that offloads part of BLAST's computation from a general-purpose processor, e.g., CPU. Illustrative, but nonlimiting, examples of processors that are known to accelerate or replace BLAST include the ASIC-based Paracel GeneMatcher™ and the FPGA-based TimeLogic DecypherBLAST™ engine.

There is also a recently developed new design for an accelerator, i.e., the FPGA-based MERCURY BLAST engine. This MERCURY BLAST engine utilizes fine-grained parallelism in BLAST's algorithms and the high input/output (I/O) bandwidth of current commodity computing systems to deliver a speedup that is at least one (1) to two (2) orders of magnitude over the software BLAST that can be deployed on a standard processor located in a laboratory.

The MERCURY BLAST engine is a multistage pipeline and this present invention involves word matching, i.e., a first stage (Stage 1), and an ungapped extension stage, i.e., a second stage (Stage 2). The present invention includes a prefilter stage between the word matching stage and the ungapped extension stage that sifts through pattern matches between a query sequence and a biological database sequence and decides whether to perform a more accurate, but computationally expensive, comparison between them. The present invention also provides a more fruitful acceleration of variable-length string matching that is robust to character substitutions. The illustrative, but nonlimiting, preferred implementation is compact, runs at high clock rates, and can process one pattern match for every clock cycle.

FIG. 1 shows a block diagram of a high level overview of a three (3) stage pipeline that is generally indicated by numeral 50. The database sequences 52 are shown entering the pipeline 50. The first stage (Stage 1) 54 provides a word matching function that detects substrings of fixed length "w" in the stream that perfectly match a substring of the query, e.g., w=11, for DNA. These short matches are also known as "w-mers." Each matching w-mer is forwarded to a second stage (Stage 2), which is an ungapped extension 56, which extends the w-mer on either side to identify a longer pair of sequences around the w-mer that match with at most a small number of mismatched characters. These longer matches are identified as high-scoring segment pairs ("HSP"s) or ungapped alignments.

Finally, every high-scoring segment pair (HSP) that has both enough matches and sufficiently few mismatches is passed to the third stage (Stage 3), which is gapped extension 58, which preferably uses the Smith-Waterman dynamic programming algorithm to extend the high-scoring segment pair (HSP) into a gapped alignment. Gapped alignment is a pair of similar regions that may differ by only a few arbitrary edits. The software, e.g., BLAST, reports only final gapped alignments with many matches and few edits 60.

Research has determined that with the standard NCBI BLASTN software program, 83.9% of the computational time was spent in the first stage (Stage 1) 54 and 15.9% of the time was spent in the second stage (Stage 2) 56. Therefore, to achieve a significant speedup, e.g., greater than six (6) times, of BLASTN would require acceleration of both the first stage (Stage 1) 54 and the second stage (Stage 2) 56. NCBI is the National Center for Biotechnology Information, which is a multi-disciplinary research group, composed of computer scientists, molecular biologists, mathematicians, biochemists, research physicians, and structural biologists concentrating on basic and applied research in computational molecular biology utilizing a variety of software databases and tools.

Figure 2:
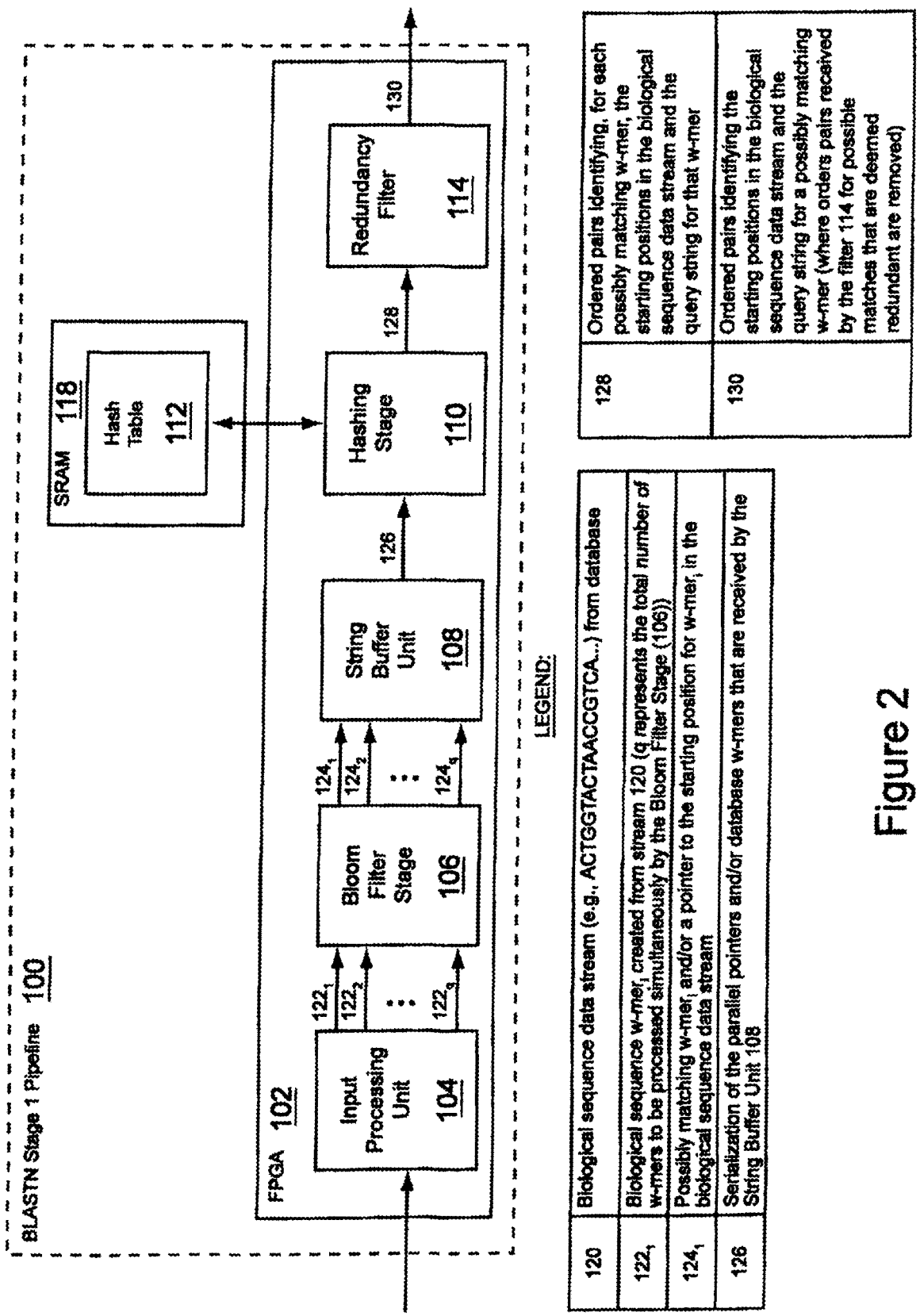
FIG. 2 provides an exemplary block diagram of a Stage 1 pipeline, e.g., BLASTN, in accordance with a preferred, nonlimiting, illustrative embodiment of the present invention.

A block diagram overview of the first stage (Stage 1) 54, referenced in FIG. 1, is shown in FIG. 2, which is a pipeline 100, e.g., BLASTN Stage 1, in accordance with a preferred embodiment of the present invention. The input processing unit 104, the Bloom filter stage 106, the string buffer unit 108, the hashing stage 110, the hash (look-up) table 112, and the redundancy filter 114 are preferably implemented on a programmable logic device. An illustrative, but nonlimiting, example of a programmable logic device 102 can include a field programmable gate array (FPGA). A hash table 112 is preferably implemented on a memory unit, e.g., static random access memory (SRAM) 118, which can be off-chip from the programmable logic device 102.

The placement of the hash table 112 as being off-chip is optional and is only a result of the memory constraints for field programmable gate arrays (FPGAs), wherein readily available FPGAs do not have sufficient capacity to store the hash table and provide the functionality of the various pipeline stages. However, if capacity for a field programmable gate array (FPGA) sufficiently increases in the future, the hash table 112 can also be implemented on an FPGA.

Figure 3:
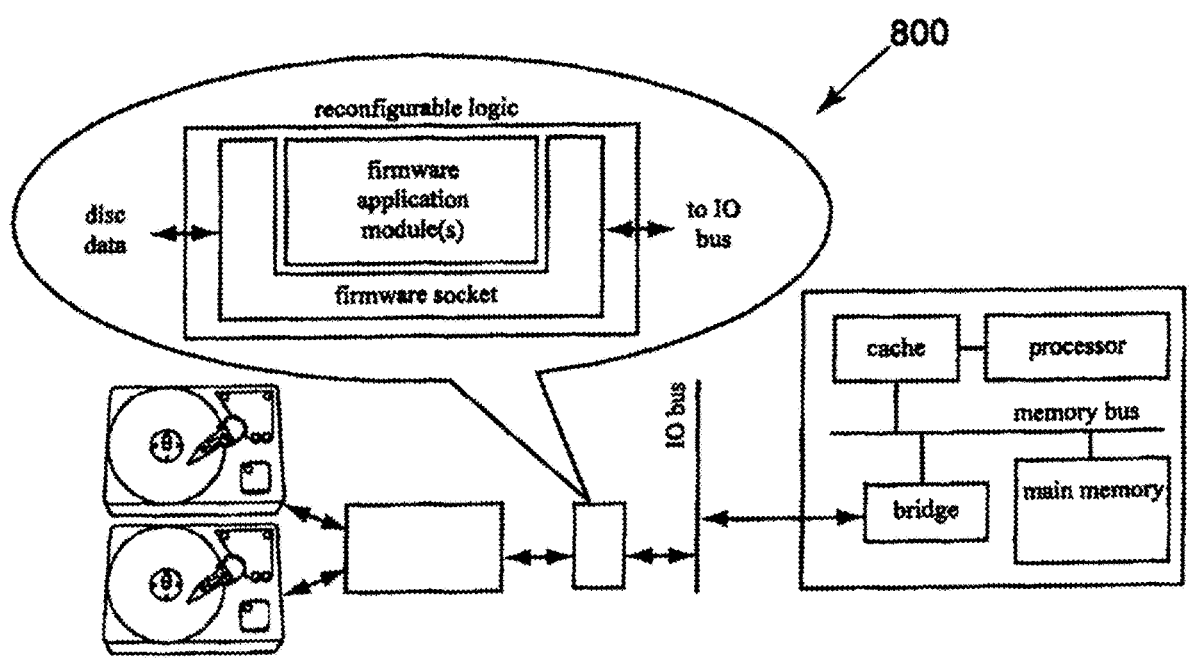
FIG. 3 is a general schematic of a hardware platform for a biological data pipeline in accordance with a preferred, nonlimiting, illustrative embodiment of the present invention.

A preferred hardware platform for pipeline 100 is that disclosed in FIG. 3 and is generally indicated by numeral 800. Additional details about this hardware platform are disclosed in: (1) U.S. Pat. No. 6,711,558 entitled "Associative Database Scanning and Information Retrieval"; (2) pending U.S. patent application Ser. No. 10/153,151, filed May 21, 2002 and entitled "Associative Database Scanning and Information Retrieval Using FPGA Devices" (published as U.S. patent application publication 2003/0018630); (3) pending PCT application PCT/US04/16398 filed May 21, 2004 and entitled "Intelligent Storage and Processing Using FPGA Devices"; and (4) a paper on "*Achieving Real Data Throughput for an FPGA Co-Processor on Commodity Server Platforms*" by Chamberlain et al., published in Proc. of 1st Workshop on Building Block Engine Architectures for Computers and Networks, Boston, Mass., October 2004; and a paper on "*Acceleration of Ungapped Extension in Mercury BLAST*" by Lancaster et al., was published on Nov. 12, 2005 for the Seventh (7th) Workshop on Media and Streaming Processors held in conjunction with the Thirty-Eighth (38th) International Symposium on Microarchitecture (MICRO-38) in Barcelona, Spain, the entire disclosures of all of which are incorporated herein by reference.

The input processing unit 104 is preferably configured to receive a biological sequence data stream 120 as an input from a sequence database, which is shown in FIG. 2. This database stream 120 represents a database sequence that can be broken down into a plurality of substrings, each substring having a base length "w." Such substrings are referred to herein as database w-mers. The input processing unit 104 preferably outputs a parallel stream of q database w-mers (or sequence w-mers) $122i$, wherein q represents the total number of database w-mers that can be simultaneously processed by the Bloom filter stage 106.

A depiction of a sample portion of a biological sequence data stream is indicated by numeral 120, which is shown in FIG. 4. Stream 120 comprises a sequence of bases (in this example, A, C, G, or T, which correspond to the bases of a DNA sequence). In this example, each base can be represented by 2 or 4 bits, as is known in the art. If w equals 11 and q equals 8, this stream 120 can be converted by the input processing unit 104 into 8 parallel w-mers as shown in FIG. 5.

The Bloom filter stage 106, as shown in FIG. 2, operates to process each database w-mer to determine whether it is a possible match with a query w-mer. A query w-mer being a substring of base length "w" derived from a query sequence. By definition, Bloom filters will not produce any false negatives between the database w-mers and the query w-mers, but Bloom filters are highly likely to produce some number of false positive matches between the database w-mers and the query w-mers. Because of the presence of these false positives, the "yes" responses of the Bloom filter to database w-mers are best referred to as possible matches.

Before processing database w-mers, the Bloom filters within Bloom filter stage 106 will need to be programmed/keyed with query w-mers from a query sequence (or query string). The query sequence is some string of bases for which a person wants to compare with the biological database sequence to find matches. The query sequence can be broken down into multiple w-mers as shown in FIG. 5 in connection with the database sequence. For a given search, the value of w is the same for both the query w-mers and database w-mers. Each Bloom filter within Bloom filter stage 106 is preferably programmed with all of the query w-mers developed from the query sequence. In an illustrative, but non-limiting, preferred embodiment, the Bloom filter stage 106 comprises a plurality of parallel Bloom filters. Also, it is preferred, but not necessary, that the parallel Bloom filters are copies of one another. A Bloom filter is said to be in parallel with another Bloom filter when both of those Bloom filters are configured to simultaneously process w-mers. Programming of the Bloom filter stage 106 can be achieved via appropriate control commands asserted by the input processing unit 104 (in response to control input to the pipeline 100).

Figure 6A:
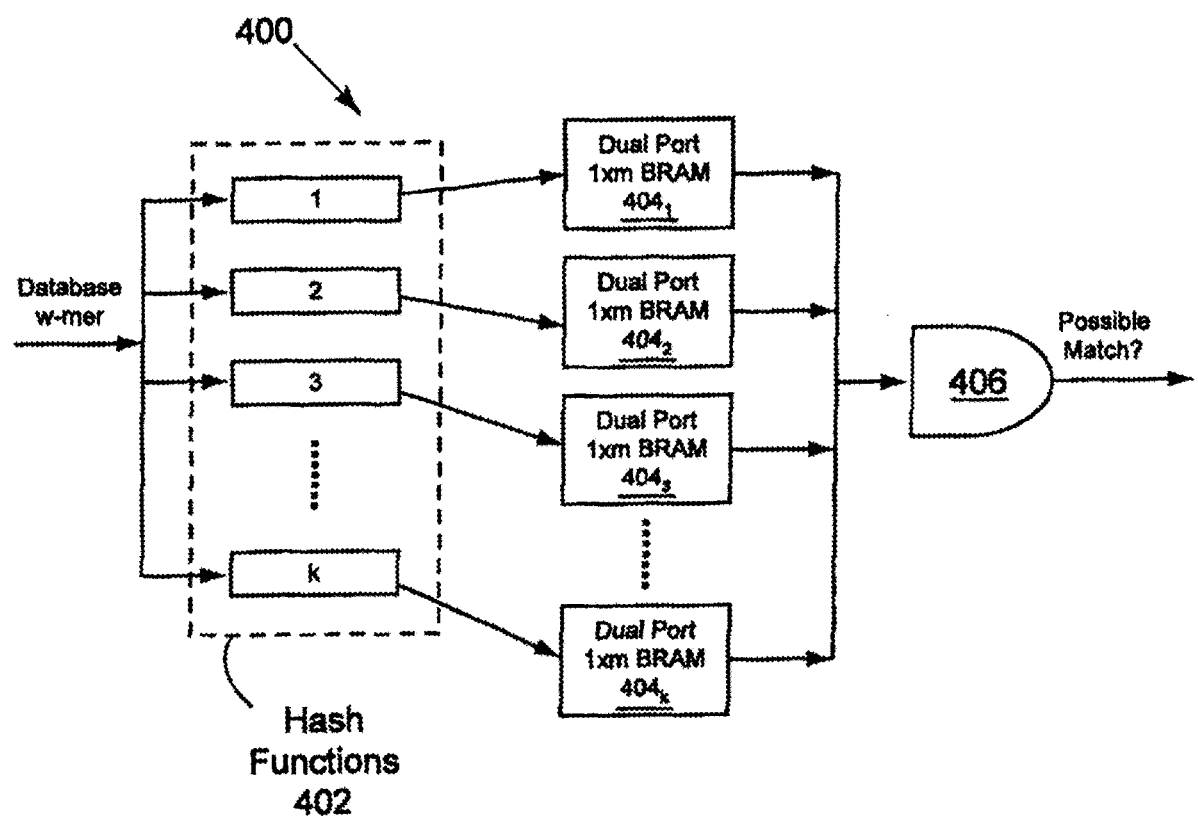
FIG. 6(a) depicts an exemplary Bloom filter stream in accordance with a preferred, nonlimiting, illustrative embodiment of the present invention.
Figure 6B:
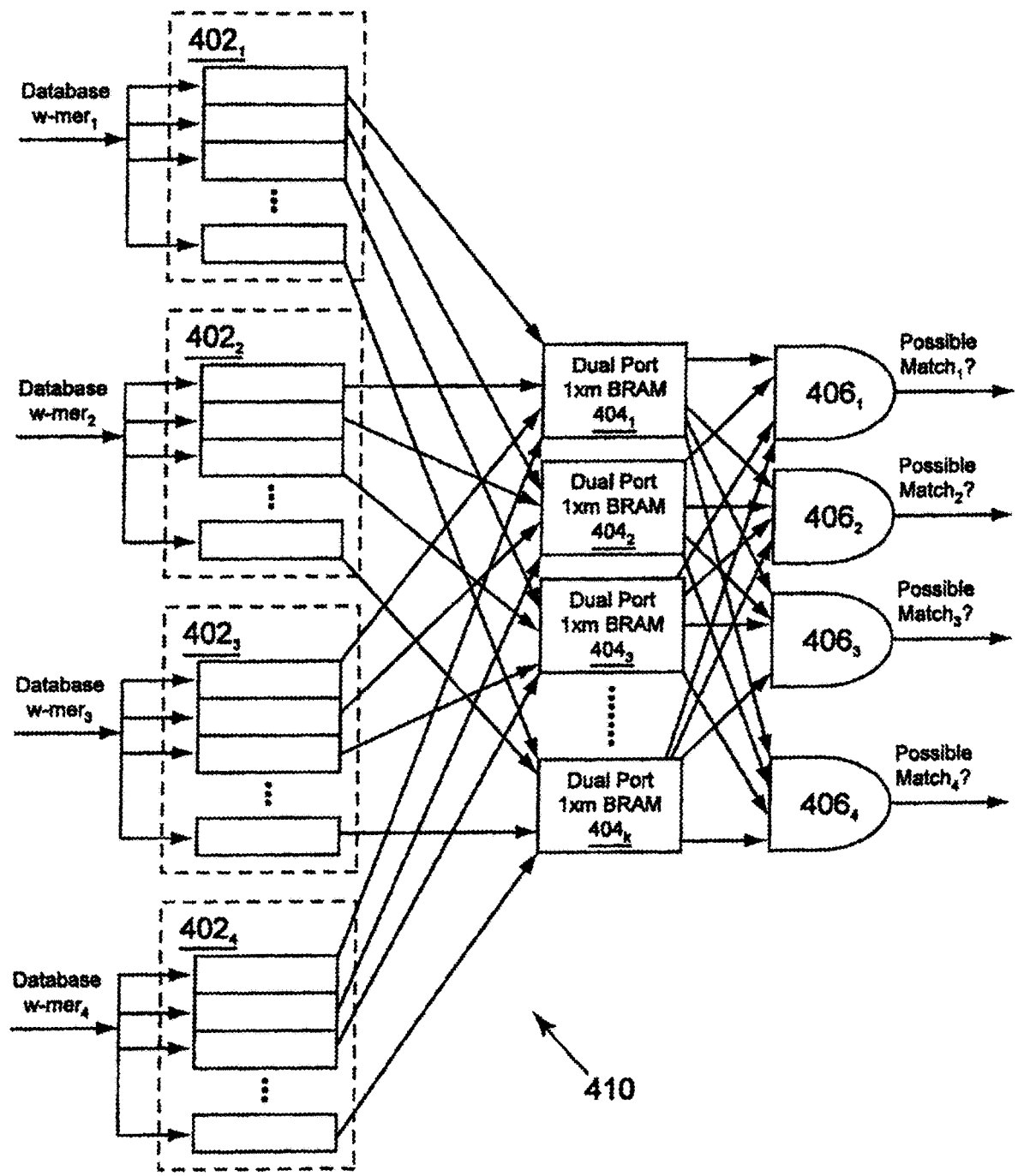
FIG. 6(b) shows an arrangement of Bloom filters configured to share the same dual port block random access memories (BRAMs) in accordance with a preferred, nonlimiting, illustrative embodiment of the present invention.
Figure 6C:
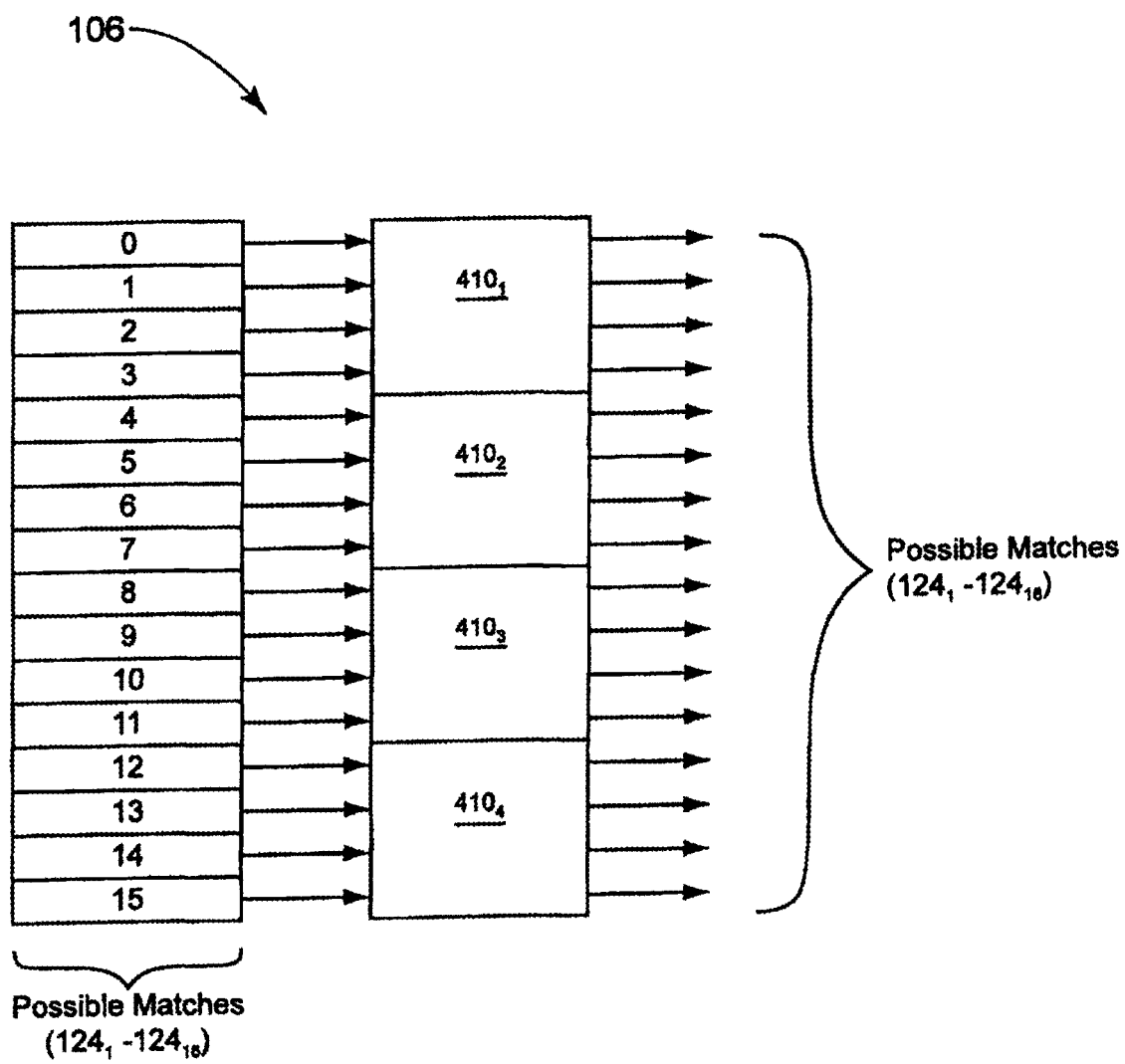
FIG. 6(c) depicts a Bloom filter stage that comprises sixteen (16) Bloom filters formed from four (4) Bloom filter arrangements, as shown in FIG. 6(b), in accordance with a preferred, nonlimiting, illustrative embodiment of the present invention.

A preferred Bloom filter architecture within the Bloom filter stage 106 is shown in FIGS. 6(a)-6(c). FIG. 6(a) depicts an exemplary Bloom filter 400. Within the Bloom filter 400, a database w-mer is processed by "k" hash functions 402, each hash function "i" operating to map the database w-mer to a bit in the 1×m dual port block RAM (BRAM) unit $404i$ that corresponds to that hash function i. If all of the bits to which that database w-mer maps within BRAMs 4041 through 404k are set (e.g., equal to 1), then logic unit 406, e.g., AND logic unit, will receive all 1's on its input lines, thereby producing a "yes" response as to whether that database w-mer is a possible match with a query w-mer.

The bits within the 1×m dual port BRAMs 404 are set if during the Bloom filter programming process, a query w-mer maps to that bit location. Because the Bloom filter is programmed with all of the query w-mers from the query sequence, the output from logic unit 406, e.g., AND logic unit, will never produce a false negative, but may produce a false positive.

The hash functions 402 are preferably the same hash functions selected from the H3 family of hash functions as used in the hashing stage 110. In the illustrative, but non-limiting, example of FIG. 6(a), the 1×m memory units 404 to which the hash functions 402 map can include dual-ported block random access memories (BRAMs). However, by virtue of being dual ported, multiple Bloom filters can share access to the same BRAM 404, thereby providing a substantial savings in the resources consumed on the programmable logic device 102, e.g., FPGA, when implementing the Bloom filter stage 106.

A description of the operation of Bloom filters can be found in U.S. patent application Ser. No. 10/640,513, which was published as U.S. Patent Application No. 2005/0086520, and was filed on Aug. 14, 2003, which is incorporated herein by reference in its entirety.

As an additional realization of consumed resources, the dual port BRAMs 404 are preferably double clocked to allow four Bloom filters 106 to share the same dual port BRAM 404. Thus, during a given clock cycle, 4 accesses can be made to each dual port BRAM 404i; thereby allowing each dual port BRAM to support four Bloom filters 106 each clock cycle.

An arrangement 410 of four (4) Bloom filters 106 configured to share the same k BRAMs 4041 through 404k is shown in FIG. 6(b). Further still, if it is feasible to triple clock the BRAMs 404, it is worth noting that each dual port BRAM 404 could support six (6) Bloom filters.

A Bloom filter stage 106 that includes at least sixteen (16) Bloom filters is shown in FIG. 6(c) formed from four (4) Bloom filter arrangements 410 that are shown in FIG. 6(b). Such a Bloom filter stage 106 is capable of simultaneously processing a different database w-mer through each parallel Bloom filter. As such, the Bloom filter stage 106 can determine whether possible matches exist for multiple (sixteen (16) in a preferred, but nonlimiting, embodiment) database w-mers simultaneously. While the Bloom filter stage 106 comprises sixteen (16) parallel Bloom filters in a preferred embodiment, it should be noted that more or less parallel Bloom filters can be used in the practice of the present invention, as would be understood by a person having ordinary skill in the art following the teachings presented herein.

Figure 7:
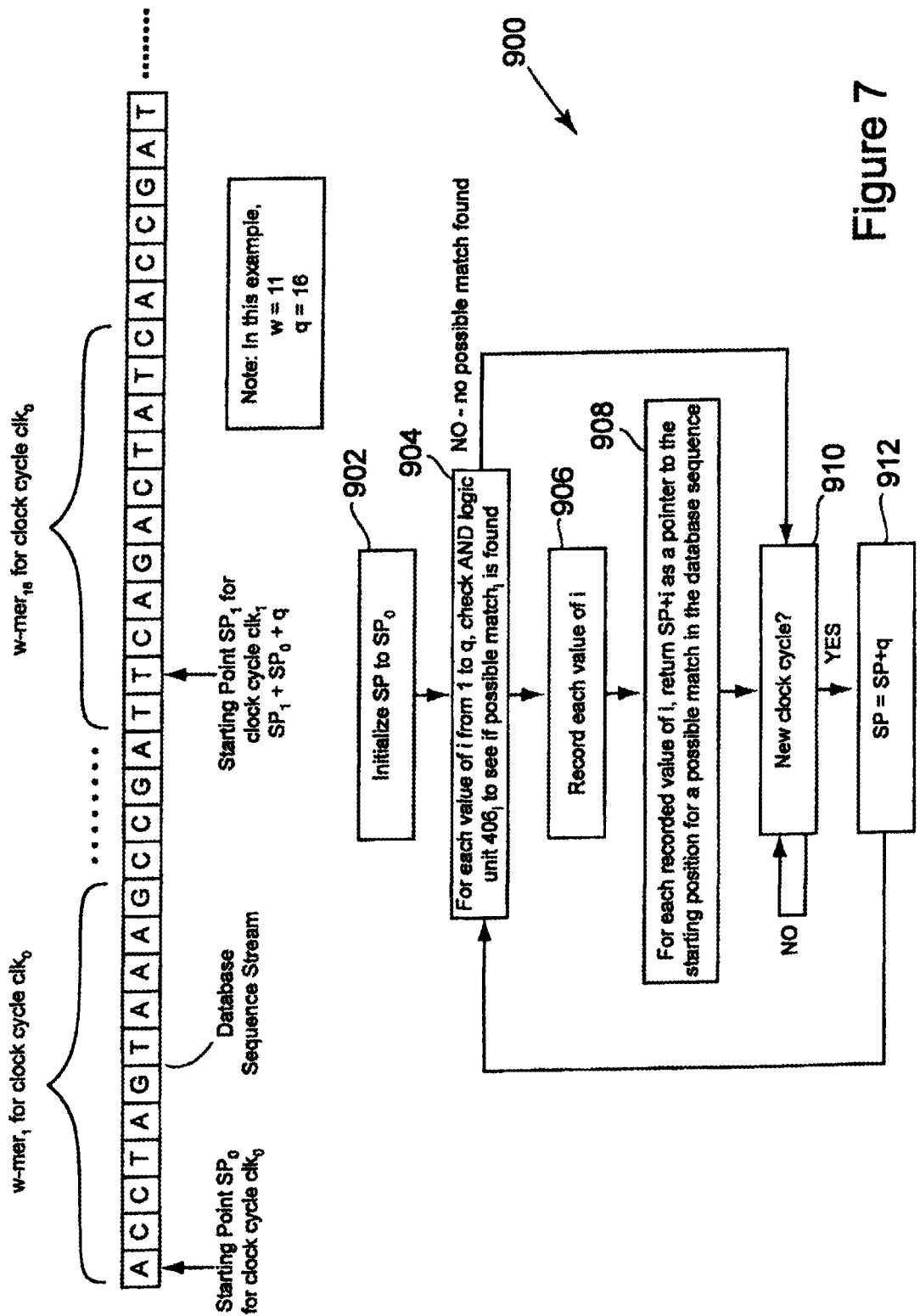
FIG. 7 is a schematic and flow chart of control logic that is either within or associated with a Bloom filter stage and readily configured to identify the starting position within the database sequence of the database w-mer that is a possible match with a query w-mer.

The control logic that is either within Bloom filter stage 106 or associated with the Bloom filter stage 106 can be readily configured to identify the starting position within the database sequence of the database w-mer that is a possible match with a query w-mer. An illustrative, but nonlimiting, example of how this control logic could be configured with an illustrative flow chart diagram is shown in FIG. 7 and is generally indicated by numeral 900. The first step is for a counter to be updated each time a new clock cycle is received to reflect the new starting point within the database sequence of w-mer for that clock cycle, as indicated by numeral 902. Depending on which logic unit 406i (or units), e.g., AND logic unit, finds a possible match 904, an appropriate starting position for a possibly matching w-mer can be recorded. If a possible match is found, then i can be recorded 906 and for each recorded value of i, return a starting point (SP) plus the value of i as the pointer for a new starting position for a possible match in the database sequence 908. The process then determines if there is a new clock cycle 910. If the answer is negative, then this determination will be repeated until there is a positive determination and the starting point (SP) can be increased by q indicated by process step 912, wherein q represents the total number of database w-mers that can be simultaneously processed by the Bloom filter stage 106. The process then returns to step 904 to determine if a possible match can be found.

If no match is found in process step 904, the process then determines if there is a new clock cycle 910. If the answer is negative, then this determination will be repeated until there is a positive determination and the starting point (SP) can be increased by q indicated by process step 912, wherein q represents the total number of database w-mers that can be simultaneously processed by the Bloom filter stage 106. The process then returns to step 904 to determine if a possible match can be found.

Each of these starting positions for a possible match is preferably then passed on to the string buffer unit 108, as shown in FIG. 2, as an output from the Bloom filter stage 106. Optionally, an output 124i from the Bloom filter stage can comprise the actual database w-mer that triggered the possible match, either in addition to or instead of the starting position pointer.

A preferred range of values for w is 5 to 15, with 11 being the most preferred value. However, it should be noted that values outside this range can also be used if desired by a practitioner of the invention. A preferred value for q is 16. A preferred value for k is 6. Preferred values for m are 32 kbits or 64 kbits. However, other values for q, k, and m can be used if desired by a practitioner of the invention. Additional details about the preferred Bloom filter stage 106 as well as alternative embodiments are described in publications that were previously incorporated by reference.

The string buffer unit 108 operates to receive the parallel outputs 1241 through 124q that comprise pointers that identify the starting position(s) in the database sequence for each database w-mer that is a possible match with a query w-mer and/or the possibly matching database w-mers themselves. String buffer unit 108 produces as an output 126 a serialized stream of pointers to these starting positions and/or possibly matching database w-mers. Additional details about the preferred string buffer unit 108 are described in publications that were previously incorporated by reference.

For each received database w-mer pointer or database w-mer within stream 126, hashing stage 110 operates to confirm that a possible match exists between a database w-mer and a query w-mer and determine a pointer to the query w-mer that may possibly match the database w-mer and is shown in FIG. 2. If stream 126 includes only pointers and not the database w-mers themselves, then it is preferred that hashing stage 110 also receive stream 120 so that the hashing stage can extract the appropriate possibly matching database w-mers from stream 120 using the starting position pointers in stream 126. Hash functions within the hash stage operate to map each possibly matching database w-mer to a position in hash table 112.

Figure 8:
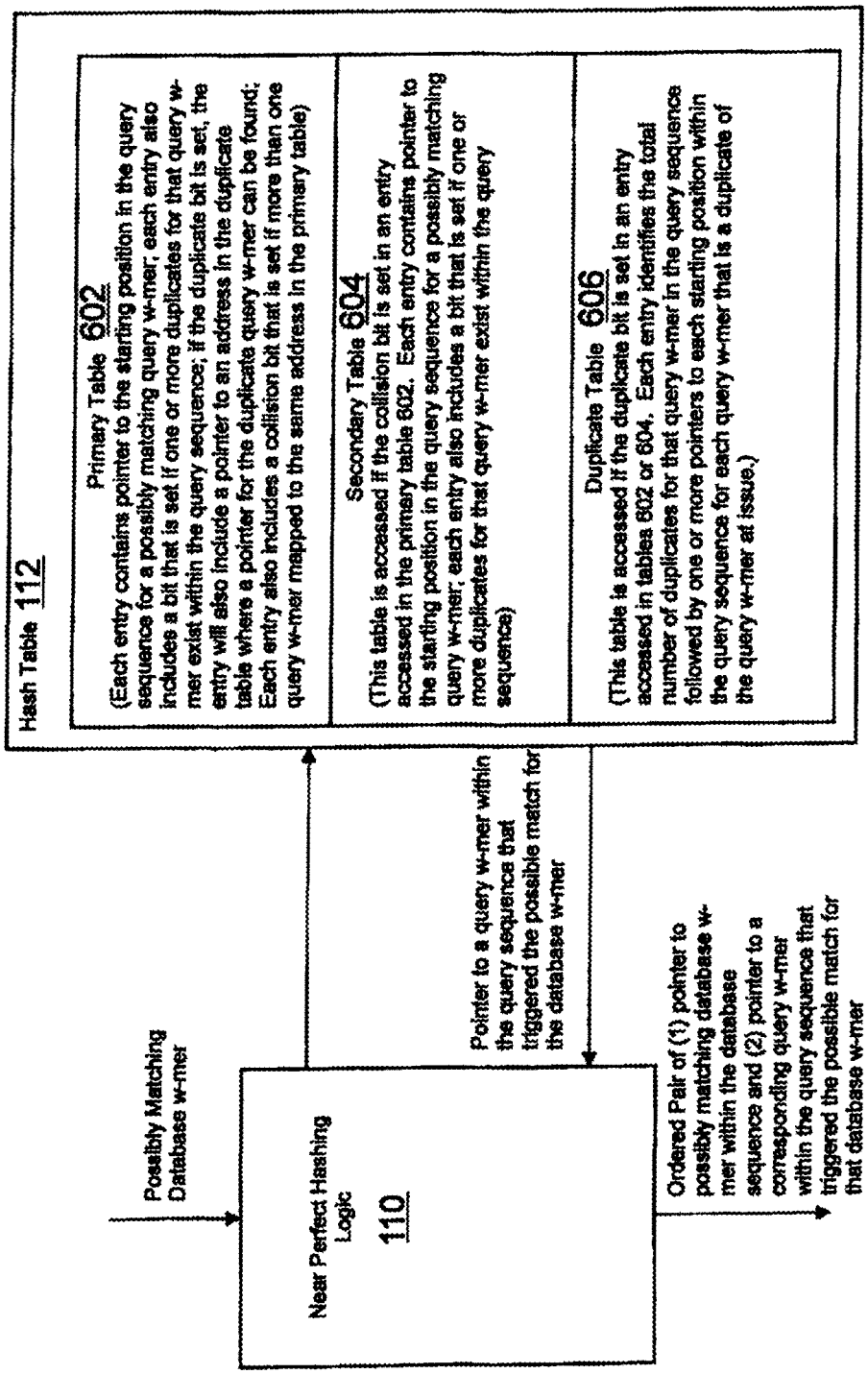
FIG. 8 illustrates an exemplary hashing stage and hash table in accordance with a preferred, nonlimiting, illustrative embodiment of the present invention.

An exemplary hashing stage 110 and hash table 112 in accordance with a preferred embodiment of the present invention is shown in FIG. 8. The hash table 112 preferably comprises a primary table 602, a secondary table 604, and a duplicate table 606. Stored at each address in primary table 602 is preferably an entry that includes a pointer to the starting position in the query sequence for the query w-mer that was mapped to that address by the hash functions for hashing stage 110. For any query w-mers that are duplicated at multiple locations within the query sequence, a duplicate bit in that query w-mer's corresponding entry in primary table 602 is preferably set.

To build the hash table 112, hash functions are used to map each query w-mer to an address in the hashing stage 110. The creation of these hash functions is preferably performed by software prior to streaming the database w-mers through the pipeline 100. Once the hash functions are created by software, these hash functions are preferably loaded into hashing stage 110 during the programming process prior to streaming the database w-mers through the pipeline. As new query biological sequences are used to program the hashing stage 110, there is a displacement table utilized by the hashing functions that is preferably updated to reflect the new query w-mers. The hashing functions themselves can remain the same. Thereafter, the hash table 112 can be programmed by processing the query w-mers through the hashing stage 110 while an appropriate control command is asserted. If desired, ordinary hash functions can be used to build the hash table 112 and process database w-mers in the hashing stage 110. However, because ordinary hashing typically produces multiple collisions, and because the hash table 112 can be stored off the programmable logic device 102, e.g., FPGA, in memory 118, e.g., SRAM, it is desirable use hashing techniques other than ordinary hashing to minimize the number of memory look-ups, and thereby avoid a potential pipeline bottleneck. In the hashing process, a collision occurs if when building a hash table 112, two different query w-mers map to the same address in the primary table 602. With ordinary hashing, such collisions are not uncommon. To resolve such collisions, a secondary table 604 is preferably used that provides different addresses for the different w-mers that mapped to the same address in the primary table 602, as is well-known. A collision bit in the address of the primary table 602 where the collision occurred is then set to identify the need to access the secondary table to properly map that w-mer.

A secondary set of hash functions are preferably used by the hashing stage 110 to map database w-mers to the secondary table 604. This secondary set of hash functions can be either ordinary hash functions, perfect hash functions, or near perfect hash functions, depending upon the preferences of a practitioner of the present invention. In a preferred hashing operation, the hash functions that map database w-mers to the primary table 602 and the hash functions that map database w-mers to the secondary table 604 simultaneously process all received database w-mers. If the address in the primary table 602 to which the database w-mer maps has its collision bit set, then the hashing stage logic uses the address in the secondary table 604 to which that database w-mer mapped, thereby avoiding the need for the hashing stage to re-hash a database w-mer if that database w-mer maps to an address where a collision occurred.

In a first alternative embodiment that seeks to minimize the number of hash table look-ups, perfect hashing functions are used to build the hash table 112 and perform the mapping of hashing stage 110. If perfect hashing is used to build hash table 112, then the secondary table 604 is not needed. Perfect hashing functions are explained in greater detail in some of the publications incorporated by reference.

In a second alternative embodiment, there is a need to reduce the number of hash table look-ups so that near perfect hashing functions are used to build the hash table 112 and perform the mapping of hashing stage 110. Near perfect hashing can be defined as hashing that operates to provide a decreased likelihood of collisions relative to the likelihood of collisions provided by ordinary hashing functions, and wherein the hashing approaches a perfect hash the longer that it executes. Near perfect hashing functions are explained in greater detail in some of the publications incorporated by reference. The preferred near perfect hashing functions are those in the family H3 chosen to be of full rank. The family of hashing functions that is designated as "H3" as well as the concept of "full rank" are fully described and disclosed in numerous publications in this area. More generally, the near-perfect hashing algorithm described herein may be used to generate a mapping of a set of binary strings of common length equal to n, referred to as keys, to indices into a hash table, so that few or no pairs of keys map to the same location in the table. The hashing logic of hashing stage 110 is preferably implemented on the programmable logic device 102, e.g., FPGA, to map possibly matching database w-mers to their respective positions in the query sequence.

If the hashing stage 110 maps a possibly matching database w-mer to an empty entry in the hash table 112, then that database w-mer can be discarded as a false positive. If the hashing stage 110 maps a possibly matching database w-mer to an entry in the hash table 112 that contains a pointer to a position in the query sequence, then neither the duplicate bit nor the collision bit will be set. Then that pointer points to the only starting position in the query sequence for the query w-mer that is a possible match to that database w-mer.

If the hashing stage 110 maps a possibly matching database w-mer to an entry in the hash table 112 for which the collision bit is set, then the hashing stage 110 looks to the address in the secondary table 604 where the secondary hash function mapped that possibly matching database w-mer. Once the proper entry in the secondary table 604 for the database w-mer is identified, then the secondary table entry is processed in the same manner as entries in the primary table (whose collision bits are not set).

If the hashing stage 110 maps a possibly matching database w-mer to an entry in the hash table 112 that contains a pointer to a position in the query sequence, and the duplicate bit is set, then that pointer points to one of a plurality of starting positions in the query sequence for the query w-mer that is a possible match to that database w-mer. To obtain the starting position(s) for each duplicate query w-mer, the duplicate table 606 is then preferably accessed. Also included in each primary table entry whose duplicate bit is set is a pointer to an address in the duplicate table 606 for that query w-mer. At that address, the duplicate table address preferably includes an entry that identifies the total number of duplicate query w-mers that exist in the duplicate table 606 for a given query w-mer. This total number is preferably followed by a contiguous array comprising, for each w-mer that is a duplicate of the query w-mer at issue, a pointer to the starting position in the query sequence for that duplicate query w-mer. Alternatively, linked list techniques can be used to chain the duplicate w-mer pointers together. Further still, the system can be configured to cancel a query sequence search if, during programming of the hash table 110, the number of duplicate w-mers in the query sequence is sufficiently large to exceed the capacity of the duplicate table 606.

Therefore, the hashing stage 110 operates to identify for each database w-mer that is a possible match to a query w-mer, the starting position in the query sequence for each query w-mer that is a possible match thereto. The preferred output 128 from the hashing stage 110 is a stream of ordered pairs, where each ordered pair comprises a pointer to the starting position in the database sequence of the database w-mer that is a possible match with a query w-mer and a pointer to a starting position in the query sequence of the query w-mer that possibly matches the database w-mer. If desired, comparison logic (not shown) can be optionally implemented on the programmable logic device 102, e.g., FPGA, following the hashing stage that operates to compare the database w-mer and query w-mer for each ordered pair to eliminate false positives.

It is worth noting that the role of the duplicate table 606 can be removed from the hash table 112 and placed either in separate memory, e.g., SRAM, or on the programmable logic device 102, e.g., FPGA, as its own pipeline stage downstream from the hashing stage 110 if desired by a practitioner of the invention.

The redundancy filter stage 114 is preferably configured to remove ordered pairs from stream 128 that are deemed redundant with other ordered pairs within stream 128. The database-to-query w-mer matches that are deemed redundant and non-redundant on the basis of a user-specified redundancy threshold N as well as the preferred design of a redundancy filter stage 114 is described in documents that were previously incorporated by reference. The output 130 from redundancy filter stage 114 is preferably a stream of ordered pairs as with stream 128, with the exception that the ordered pairs for matches that are deemed redundant with other ordered pairs are not present therein.

Also, it is worth noting that the implementation on an FPGA of the FPGA pipeline stages for the programmable logic device 102 described herein is within the skill of a person having ordinary skill in the art following the teachings herein and the teachings of (1) U.S. Pat. No. 6,711,558 entitled "Associative Database Scanning and Information Retrieval"; (2) pending U.S. patent application Ser. No. 10/153,151, filed May 21, 2002 and entitled "Associative Database Scanning and Information Retrieval Using FPGA Devices" (published as U.S. patent application publication 2003/0018630); and (3) pending PCT application PCT/US04/16398 filed May 21, 2004 and entitled "Intelligent Storage and Processing Using FPGA Devices"; the entire disclosures of all of which have been incorporated herein by reference. For example, see the description for FIG. 8 in PCT application PCT/US04/16398.

After the first stage (Stage 1) for word matching 54, being accelerated, as previously described and shown in FIG. 1, the performance of the second stage (Stage 2) that relates to the ungapped extension 56 directly determines the performance of the overall pipelined application.

The purpose of extending a w-mer is to determine, as quickly and accurately as possible, whether the w-mer arose by chance alone, or whether it may indicate a significant match. Ungapped extension in the second stage (Stage 2) 56 must decide whether each w-mer emitted from word matching is worth inspecting by the more computationally intensive, gapped extension. It is important to identify and discard spurious w-mers as early as possible in the BLAST pipeline because later stages are increasingly more complex. There exists a delicate balance between the stringency of the filter and its sensitivity, i.e. the number of biologically significant alignments that are found. A highly stringent filter is needed to minimize time spent in fruitless gapped extension, but the filter must not discard w-mers that legitimately identify long query-database matches with few differences. In the illustrative, but nonlimiting, embodiment of an implementation of a programmable logic device 102, e.g., FPGA, this filtering computation must also be parallelizable and simple enough to fit in a limited area.

The implementation of the second stage (Stage 2) 56 builds on the concepts utilized in the implementation of the first stage (Stage 1) 54 described above and disclosed in P. Krishnamurthy, J. Buhler, R. D. Chamberlain, M. A. Franklin, K. Gyang, and J. Lancaster, *Biosequence Similarity Search On The Mercury System*, In Proceedings of the 15th IEEE International Conference on Application-Specific Systems, Architectures, and Processors (ASAP04), Pages 365-375 (2004), which is incorporated herein by reference in its entirety.

The second stage (Stage 2) 56 deploys an ungapped extension stage utilizing a programmable logic device, e.g., FPGA 74, which operates as a prefilter stage. This design utilizes the speed of the implementation of the programmable logic device, e.g., FPGA 74, to greatly reduce the number of w-mers passed to software while retaining the flexibility of the software implementation on those w-mers that pass in the pipeline 70.

Preferably, but not necessarily, a w-mer must pass the second stage (Stage 2) 56 ungapped extension, which may utilize both hardware and software, before being released to the third stage (Stage 3) gapped extension 58. By focusing on data streaming nature of the application with overall throughput and not latency, the addition of another processing stage is very useful.

Utilizing a first illustrative software program, e.g., NCBI BLASTN, the second stage (Stage 2) 56 is now described. The ungapped extension of a w-mer into an HSP runs in two steps utilizing NCBI BLASTN. The w-mer is extended back toward the beginnings of the two sequences, then forward toward their ends. As the HSP extends over each character pair, that pair receives a reward $+\alpha$ if the characters match or a penalty $-\beta$ if they mismatch. An HSP's score is the sum of these rewards and penalties over all its pairs. The end of the HSP in each direction is chosen to maximize the total score of that direction's extension. If the final HSP scores above a user-defined threshold, it is passed on to the third stage (Stage 3), gapped extension 58.

For long biological sequences, it is useful to terminate ungapped extension before reaching the ends of the sequences, especially if no high scoring HSP is likely to be found. In the illustrative software, BLASTN, implements early termination by an X-drop mechanism. The algorithm tracks the highest score achieved by any extension of the w-mer thus far; if the current extension scores at least X below this maximum, further extension in that direction is terminated. Ungapped extension with X-dropping allows the BLASTN software to recover HSPs of arbitrary length while limiting the average search space for a given w-mer. However, because the regions of extension can in principle be quite long, this heuristic is not as suitable for fast implementation in a typical programmable logic device 74, e.g., FPGA. Note that even though extension in both directions can be done in parallel, this was not sufficient to achieve a desired speedup on processing.

The prior processing of the second stage (Stage 2) 56 utilizing ungapped extension is shown in FIG. 9 utilizing NCBI BLAST. The parameters used here are w=5, $\alpha=1$, $\beta=-3$, and X-drop=10. W is the length of a substring, $\alpha$ is a positive reward for character match, $\beta$ is a negative penalty for character mismatch and X-drop is the reduction below the maximum level of current extension scores where further extension is terminated. The use of X-dropping allows the software to recover HSPs of an arbitrary length while limiting the average search space for a given w-mer but it is still not very fast or efficient.

The ungapped extension analysis with a preferred software program, i.e., NCBI BLAST, is generally indicated by numeral 62 and begins at the end of the w-mer and extends left. The extension stops when the running score drops 10 below the maximum score (as indicated by the arrows). This is also indicated as the user modifiable "X-drop" parameter. The same computation is then performed in the other direction. The final substring is the concatenation of the best substrings from the left and right extensions.

Figure 12:
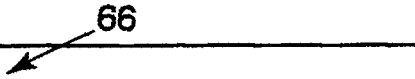
FIG. 12 is an illustrative, but nonlimiting, listing of pseudocode utilized in an ungapped extension algorithm in accordance with a preferred, nonlimiting, illustrative embodiment of the present invention.
Figure 20:
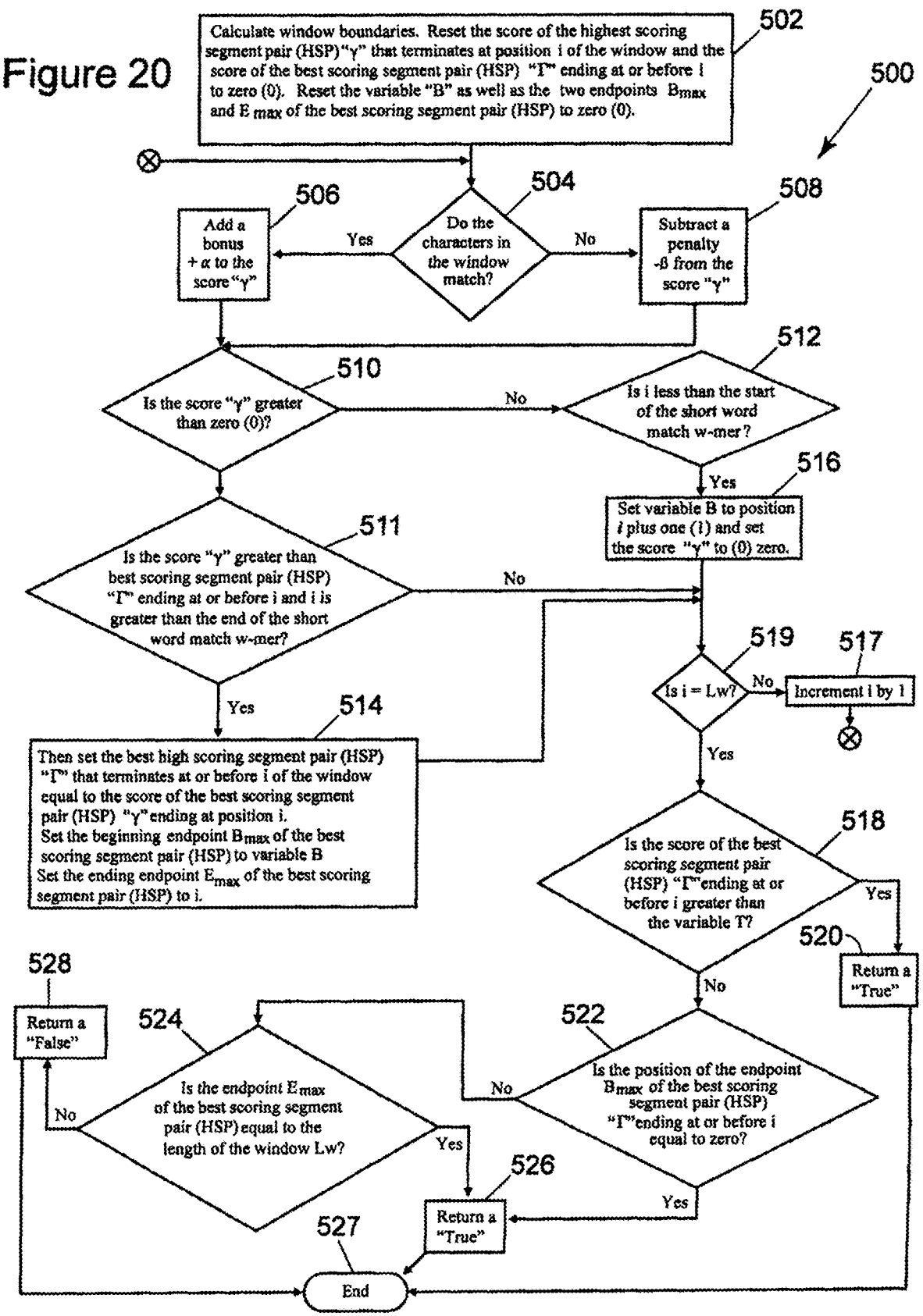
FIG. 20 is a flow chart of the algorithm shown in FIG. 12 utilized in an ungapped extension in accordance with a preferred, nonlimiting, illustrative embodiment of the present invention.

In the present invention, a prefilter is utilized to improve processing efficiency. The extension algorithm for a given w-mer is performed in a single forward pass over a fixed size window. This extension begins by calculating the limits of a fixed window of length $L_w$, which is centered on the w-mer in both the query and database stream. Afterward, the appropriate substrings of the query and the database stream are then fetched into buffers. Once the substrings are buffered, then the extension algorithm begins. The extension algorithm in pseudo code is shown on FIG. 12 and generally indicated by numeral 66 and the associated flow chart is shown on FIG. 20 and is generally indicated by numeral 500. This algorithm 66 also lends itself to hardware implementation despite the sequential expression of the computation.

This prefilter extension algorithm implements a dynamic programming recurrence that simultaneously computes the start and end of the best high-scoring segment pair (HSP) in a predetermined window. The first step 502 is to calculate predetermined window boundaries. The current position within a window is indicated by a variable "i". There is then a reset of the score "γ" of the best high-scoring segment pair (HSP) that terminates at position i of the window and the score "Γ" of the best high-scoring segment pair (HSP) ending at or before i to zero (0). This is followed by a reset of the variable "B" as well as the two endpoints Bmax and Emax of the best high scoring segment pair (HSP) ending at or before i to the value of zero (0).

First, for every position i in a window up to the length of the window $L_w$, a determination is made as to whether characters in the window match 504 and the score contribution of each character pair in the window is computed, using a reward +α, indicated by numeral 506 and a penalty –β, indicated by numeral 508 as the implementation for providing rewards for pattern matches and penalties for pattern mismatches, respectively. These contributions can be calculated independently in parallel for each pair. If there is a reward +α, it is added to the score γ, i.e., γ=γ+α. and if there is a penalty –β, it is subtracted from the score, i.e., γ=γ–β.

Then, the algorithm determines if the score γ of the best high-scoring segment pair (HSP) is greater than zero (0) 510. If this determination is positive, then there is a determination if the score "γ" of the best high-scoring segment pair (HSP) that terminates at position i of the window is greater than the score "Γ" of the best high-scoring segment pair (HSP) ending at or before i and if i (position in the window) is greater than the end of a short word match w-mer (WmerEnd) 511.

If this determination in step 510 is negative, then there is a determination of whether i is less than the start of the short word match w-mer (WmerStart) 512. If i is less than the start of the short word match w-mer, then the variable B is set to the current position within a window i incremented by one (1) and the score "γ" of the best high-scoring segment pair (HSP) is set to (0) zero 516. The next step is then a determination if i is equal to the length of the window $L_w$ 519. If the determination in step 511 is positive, then the score "Γ" of the best high-scoring segment pair (HSP) ending at or before i is set to the score "γ" of the best high-scoring segment pair (HSP) that terminates at i, the endpoint $B_{max}$ of the best high-scoring segment pair (HSP) "Γ" ending at or before i is set to the variable B and the endpoint Emax of the best high-scoring segment pair (HSP) is set to i (position in the window) 514. The next step is then a determination if i is equal to the length of the window $L_w$ 519. Moreover, if the determination in step 511 is negative, then there is also a determination if i is equal to the length of the window $L_w$ 519.

If the determination in step 519 is negative, then the variable i is incremented by one (1) in step 517 and the process is returned to step 504. If this determination in step 519 is positive, then the software program proceeds to the next program step 518, which is a determination whether the score of the best high-scoring segment pair (HSP) "Γ" is greater than the variable T in step 518. If this determination is positive, then a value of "true" is returned 520 and the software program ends 527.

If the determination in step 518 is negative, this is followed by a determination of whether the position of the endpoint Bmax of the best high-scoring segment pair (HSP) is equal to zero 522. If this determination is positive, then a value of "true" is returned 526 and the software program ends 527.

Finally, if the determination in step 522 is negative, there is a determination of whether the endpoint $E_{max}$ of the best high-scoring segment pair (HSP) is equal to the length of the window $L_w$ 524. If this determination is positive, then a value of "true" is returned 526 and the algorithm ends 527 and if this determination is negative, then a value of "false" is returned 528 and the algorithm will again end 527.

In summary, the algorithm tracks Γ, which is the score of the highest scoring HSP ending before i, along with its endpoints $B_{max}$ and $E_{max}$. Therefore, if $\Gamma_{Lw}$ is greater than a user-defined threshold score, the w-mer passes the prefilter and is forwarded to (Stage 2b) 84 for the ungapped extension.

There are two aspects of this prefilter algorithm. The first aspect is that the recurrence requires that the HSP found by the algorithm pass through its original matching w-mer and that a higher-scoring HSP in the window that does not contain this w-mer is ignored. This constraint ensures that, if two distinct biological features appear in a single window, the w-mers generated from each have a chance to generate two independent HSPs. Otherwise, both w-mers might identify only the feature with the higher-scoring HSP, causing the other feature to be ignored.

The second aspect is if the highest scoring HSP intersects the bounds of the window, it is passed on to software regardless of the score. This heuristic ensures that HSPs that might extend well beyond the window boundaries are properly found by software, which has no fixed size window limits, rather than being prematurely eliminated.

Figure 10:
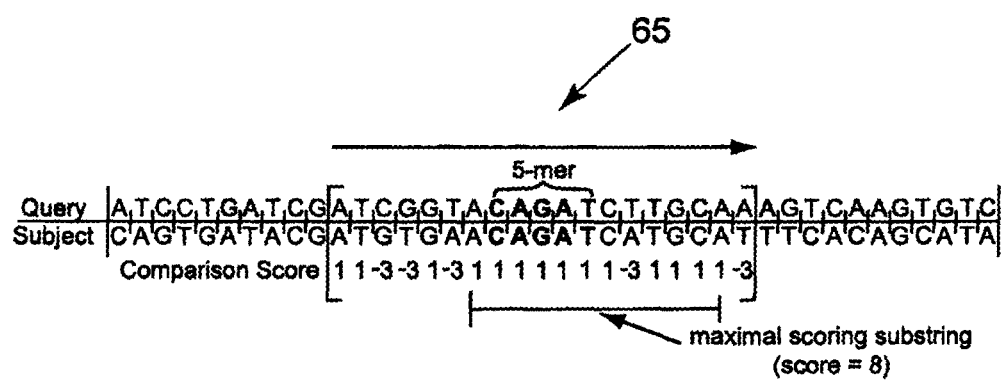
FIG. 10 depicts an exemplary data window associated with the analysis of ungapped extension with analysis in a single direction within a predefined data window in accordance with a preferred, nonlimiting, illustrative embodiment of the present invention.

An illustrative example of the ungapped extension prefilter utilizing the illustrative Mercury BLAST is shown in FIG. 10. Using the same parameters of FIG. 9 with the addition of a new parameter $L_w$, which is the length of a predetermined window, then $L_w$=19, w=5, α=1, β=–3, the present invention, e.g., Mercury BLAST, ungapped extension, as generally indicated by numeral 65, begins at the leftmost base of the window (indicated by brackets) and moves right, calculating the best-scoring substring in the window. In this example, the algorithms gave the same result in both FIGS. 9 and 10. However, this is not necessarily the situation in general.

Figure 11:
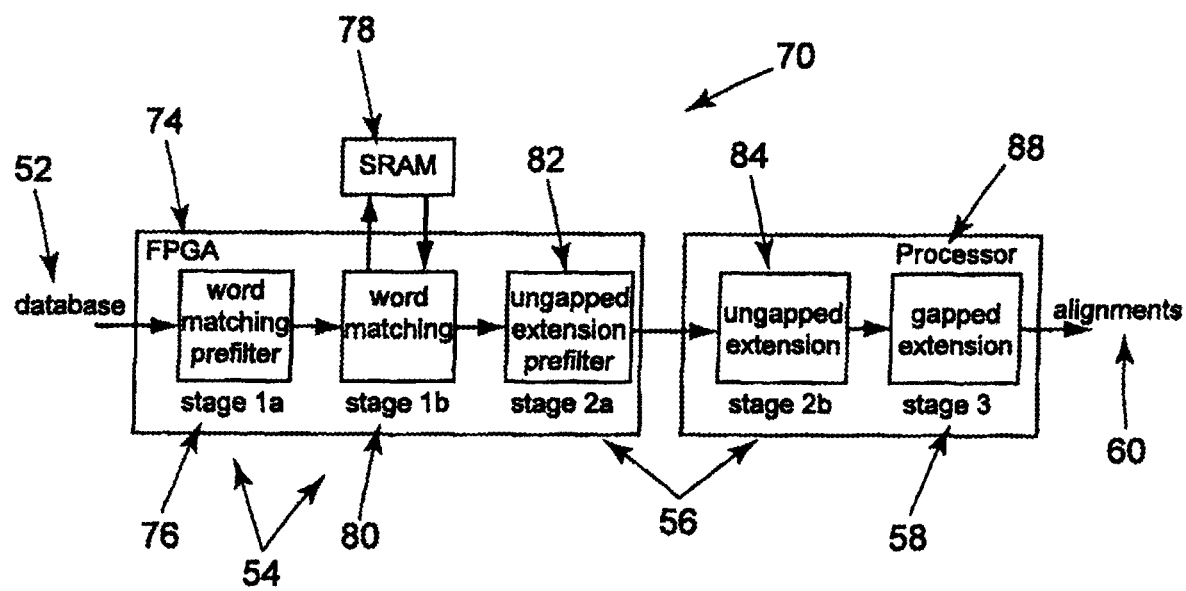
FIG. 11 is a block diagram overview of the three (3) stage pipeline of FIG. 1, wherein the first and second stages are each broken down into two (2) substages.

An illustrative system of the present invention is shown in schematic form as the application pipeline and is generally indicated by numeral 70 is shown in FIG. 11. This system is preferably an infrastructure designed to accelerate disk-based computations and exploits the high input/output (I/O) bandwidth available from modern disks by streaming data 52 directly from the disk medium to programmable logic devices such as, but not limited to, FPGAs (field programmable gate arrays) 74.

The streaming data is delivered to the hardware word matching prefilter 76, which is designated as Stage 1a. After the data stream is prefiltered, it passes into a word matching module 80, as previously described above and is designated as Stage 1b. The word matching module 80 utilizes memory 78, e.g., SRAM (static random access memory that retains data bits in its memory as long as power is being supplied and does not have to be periodically refreshed). The combination of Stage 1a and 1b, 76 and 80 form the previously described first stage (Stage 1) 54, that was previously shown in FIG. 1.

The data then passes into an ungapped extension prefilter 82 which includes dedicated hardware and/or firmware, which is designated as Stage 2a. The output of the prefilter then passes into the remainder of Stage 2, which is the ungapped extension 84, which is designated as Stage 2b and includes software. The combination of Stage 2a and 2b, 82 and 84 form the previously described second stage (Stage 2) 56, previously shown in FIG. 1.

Figure 11A:
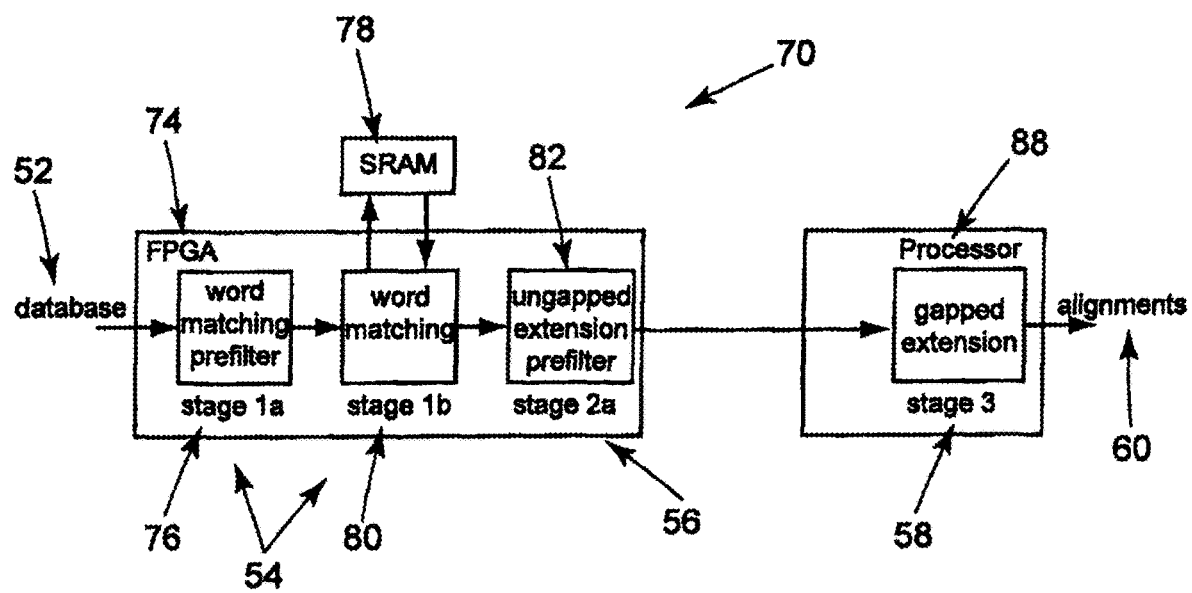
FIG. 11A is a block diagram overview of the three (3) stage pipeline of an alternative embodiment of the present invention shown in FIG. 1, wherein only the first stage is broken down into two (2) substages.

In the alternative, if there are enough hardware/firmware resources available, the software ungapped extension 84, which is designated as Stage 2b, can be eliminated with the hardware/firmware ungapped extension prefilter 82 functioning as the sole ungapped extension, which is designated as Stage 2 and shown in FIG. 11A. This methodology can provide higher throughput since the software portion of the ungapped extension can be eliminated in the utilization of the biological sequence similarity search computation, e.g., BLAST, search.

The data stream finally passes into the gapped extension 58, which is designated as Stage 3. The ungapped extension and gapped extension can be operated by a wide variety of computing mechanisms, including, but not limited to, a processor 88. The prefilter (Stage 2a) 82 lends itself to hardware implementation despite the sequential expression of the computation in FIG. 12.

The ungapped extension prefilter design 82 is fully pipelined internally and accepts one match per clock. The prefilter is parameterizable with the parameters chosen based on a number of design-specific constraints. The commands are supported to configure parameters such as a match score, a mismatch score, and a cutoff threshold. Therefore, there is a trade-off between sensitivity and throughput that is left to the discretion of the user.

Figure 13:
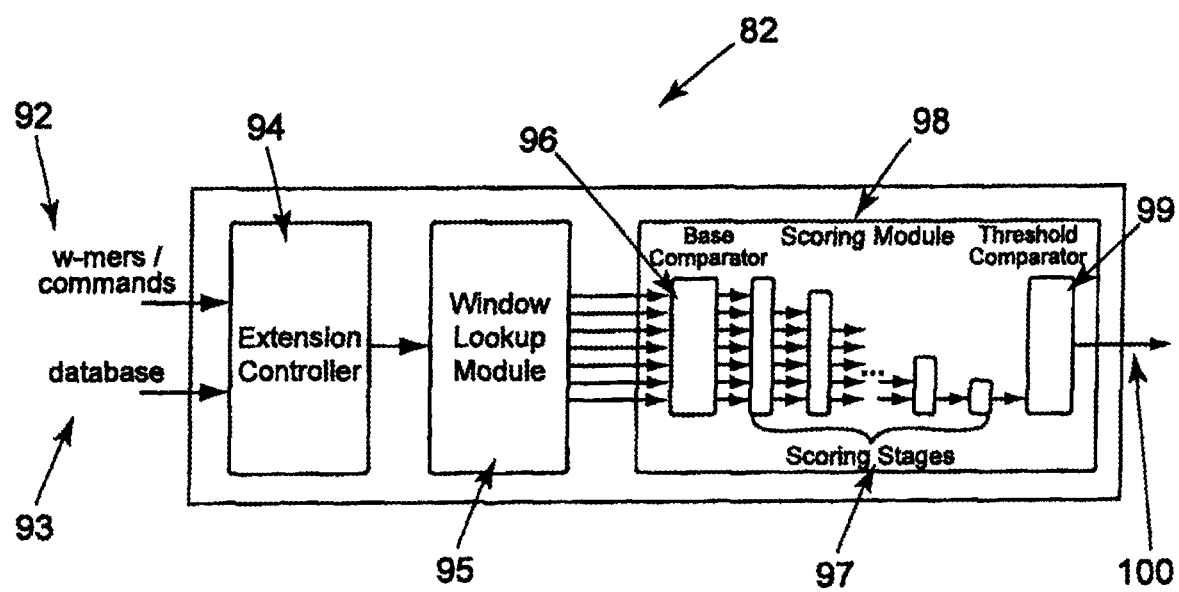
FIG. 13 is an illustrative, but nonlimiting, block diagram of a prefilter stage for an ungapped extension in accordance with a preferred, nonlimiting, illustrative embodiment of the present invention.

Since the w-mer matching stage generates more output than input, two independent data paths are used for input into the ungapped extension, i.e., Stage 2a, which is generally indicated by numeral 82 and is shown in FIG. 13. The w-mers/commands and the data are parsed with the w-mers/commands are received on one path 92, and the data from the database is received on the other path 93. The commands are supported by an active control valid signal and the commands are also transmitted in a predetermined format. Also, the commands are designed so that the programmable logic device 74, e.g., FPGA, shown in FIG. 11, does not need to be reconfigured.

The module is organized into three (3) pipelined stages. This includes an extension controller 94, a window lookup module 95 and a scoring module 98. There is an extension controller 94 that parses the input to demultiplex the shared w-mers command 92 and database stream 93. All w-mer matches and the database stream flow through the extension controller 94 into the window lookup module 95. The window lookup module 95 is the module that is responsible for fetching the appropriate substrings of the database stream and the query to form an alignment window.

Figure 13A:
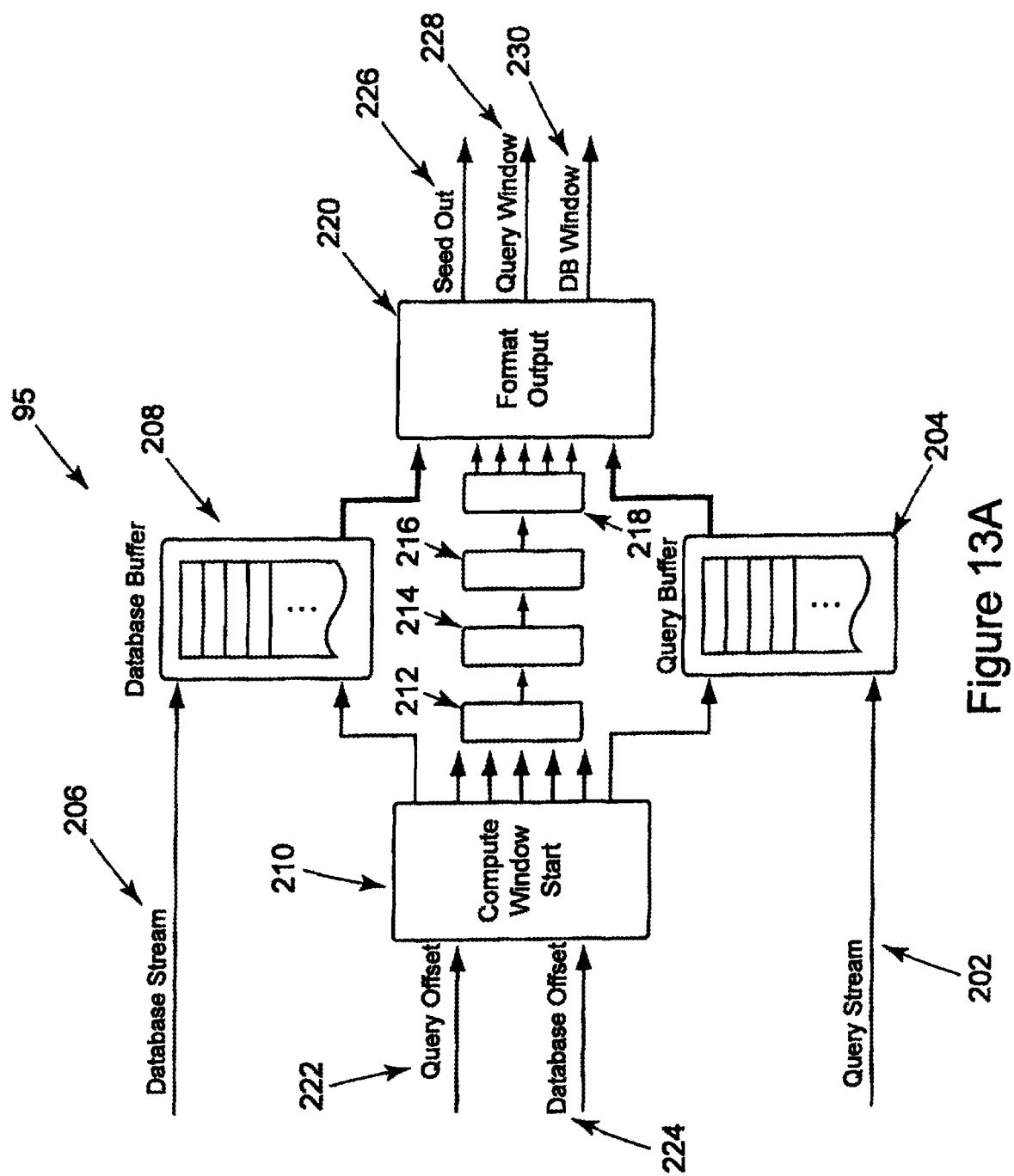
FIG. 13A is an illustrative, but nonlimiting, block diagram of a window lookup module of the prefilter stage for an ungapped extension, as shown in FIG. 13.

The window lookup module 95 is illustrated in additional structural detail in FIG. 13A. Preferably, but not necessarily, a query is stored on-chip utilizing dual-ported random access memory (RAM) on the programmable logic device 74, e.g., FPGA, shown in FIG. 11. The query is streamed 202 at the beginning of each biological sequence similarity search computation, e.g., BLAST search, and is fixed until the end of the database is reached. The size of the query stream 202 is limited to the amount of memory, e.g., block random access memories (RAMs) that are provided in the query buffer 204. The database is also streamed 206 in a similar manner as the query stream 202 and provided to a database buffer 208. The database buffer 208 is preferably, but not necessarily, a circular buffer. The use of a circular buffer is helpful to retain a necessary section of the database stream 206 that any windows that are formed from the arriving w-mers might require. Since the w-mer generation is performed in the first stage 54, as shown in FIG. 1, only a small portion of the database stream 206 needs to be buffered in the database buffer 208 in order to accommodate each extension request.

The database buffer 208 is preferably, but not necessarily, built to allow a fixed distance of w-mers that are out-of-order to be processed correctly. For the previously referenced BLASTP implementation, this is important since the w-mers in the word matching stage 80, as shown in FIG. 11, will possibly be out-of-order.

The window lookup module 95 preferably, but not necessarily, is organized as a six (6) stage pipeline that is shown in FIG. 13A. This includes a first stage 210, a second stage 212, a third stage 214, a fourth stage 216, a fifth stage 218 and a sixth stage 220. Extensive pipelining may be necessary to keep up with requests from the previous stage, i.e., extension controller 94 shown in FIG. 13, which may come once per clock pulse.

The first stage of the pipeline 210 calculates the beginning of the query and database windows based on the incoming w-mer and a configurable window size. The offset of the query 222 and the offset of the database 224 is provided to the first stage 210. This first stage of the pipeline 210 calculates the beginning of the query window and database windows based on the incoming w-mer and a configurable window size. The offset of the beginning of the window is then passed to the buffer modules, i.e., the second stage 212, the third stage 214, the fourth stage 216 as well as the fifth stage 218, which begins the task of reading a superset of the window from memory, e.g., block RAMs. An extra word of data must be retrieved from the memory, e.g., block RAMs, because there is no guarantee that the window boundaries will fall on a word boundary. Therefore, an extra word is fetched on each lookup so that the exact window can be constructed from a temporary buffer holding a window size worth of data plus the extra word. The next four (4) stages, i.e., the second stage 212, the third stage 214, the fourth stage 216 and the fifth stage 218, move the input data lock-step with the buffer lookup process and ensure that pipeline stalls are handled in a correct manner. Finally, the superset of the query and database windows arrive to the final stage or sixth stage for format output 220. The output includes a seed out 226, a query window 228 and a database window 230 so that the correct window of the buffers is extracted and registered as the output.

In an illustrative, but nonlimiting, embodiment, the query is buffered on-chip using the dual-ported block random access memory (BRAM) on to programmable logic devices such as, but not limited to, FPGAs (field programmable gate arrays) 74, as shown in FIG. 11. Preferably, but not necessarily, the database stream is preferably buffered in a circular buffer, which can be created from BRAMs. As previously mentioned, the w-mer generation is done in the first stage for the extension controller 94. Only a small amount of the database stream 93 needs to be buffered to accommodate each input w-mer because they arrive from Stage 1a, 76, and Stage 1b, 80, in order with respect to the database stream 93.

Since the illustrative, but nonlimiting, dual-ported block random access memories (BRAMs) are a highly-utilized resource in Stage 1a, 76, and Stage 1b, 80, the memories, e.g., dual-ported block random access memories BRAMs, are time-multiplexed to create a quad ported BRAM structure. After the window is fetched, it is passed into the scoring module 98 and stored in registers. The scoring module 98 implements the recurrence of the extension algorithm 66 on FIG. 12. Since the computation is too complex to be done in a single cycle, the scorer is extensively pipelined.

Figure 14:
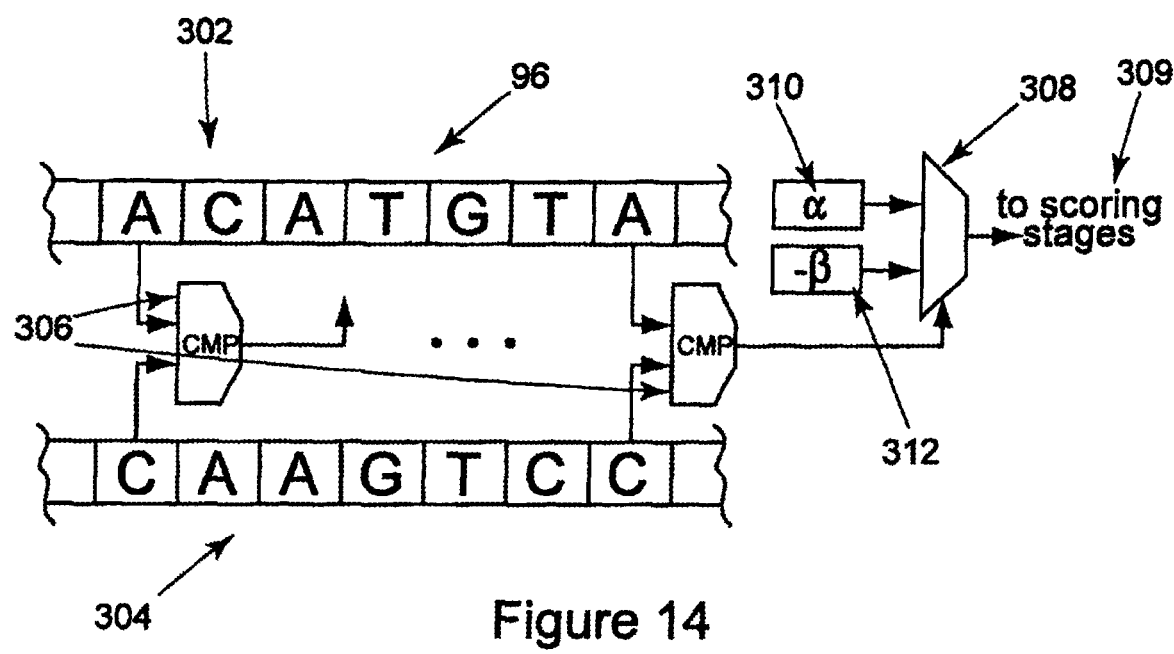
FIG. 14 is an illustrative, but nonlimiting, block diagram of a base comparator, as shown in FIG. 13, in accordance with a preferred, nonlimiting, illustrative embodiment of the present invention.

The first stage of the scoring pipeline 98 is shown in FIG. 13. The base comparator 96 receives every base pair in parallel registers as shown by numerals 302 and 304, respectively as shown in FIGS. 13 and 14. These pairs are fed into a plurality of comparators 306 that assign a comparison score to each base pair in the window. In the illustrative but preferred embodiment, for DNA sequences, e.g., BLASTN, the base comparator 96 assigns a reward +α, generally indicated by numeral 310, to each matching base pair and a penalty −β, generally indicated by numeral 312 to each mismatching pair. The score computation is the same for protein sequence analysis, e.g., BLASTP, except there are many more choices for the score. In BLASTP, the reward +α and the penalty −β are replaced with a value from a lookup table that is indexed by the concatenation of the two symbols 302, 304. The calculation of all of the comparison scores is performed in a single cycle using $L_w$ comparators. After the scores are calculated, the calculated scores are delivered to later scoring stages 309.

The scoring module 98 is preferably, but not necessarily, arranged as a classic systolic array. The data from the previous stage are read on each clock pulse and results are output to the following stage on the next clock pulse. Storage for comparison scores in successive pipeline stages 97 decrease in every successive stage and is shown in FIG. 13. This decrease is possible because the comparison score for window position "i" is consumed in the ith pipeline stage and may then be discarded, since later stages inspect only window positions that are greater than i.

Figure 15:
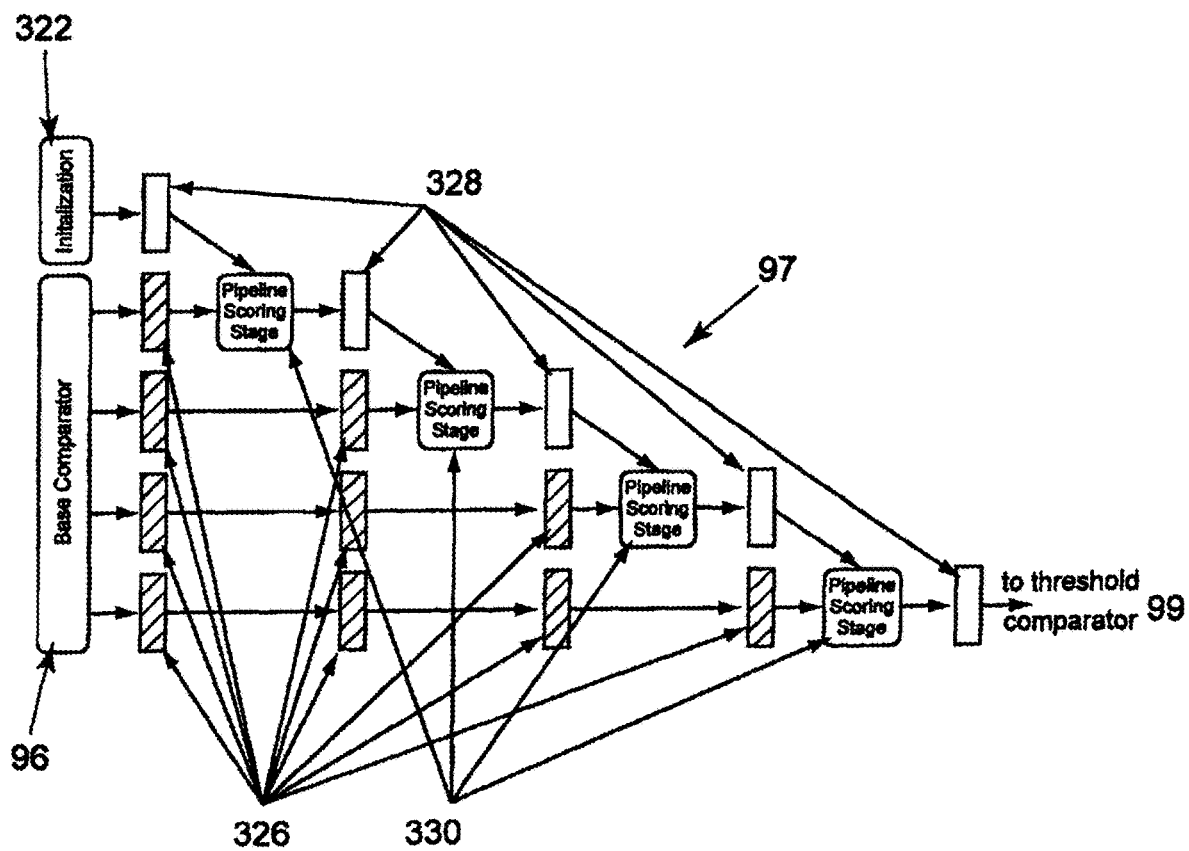
FIG. 15 is an illustrative, but nonlimiting, block diagram of an array of scoring stages, as shown in FIG. 13, in accordance with a preferred, nonlimiting, illustrative embodiment of the present invention.

This structure of data movement is shown in more detail in FIG. 15, which is generally indicated by numeral 97 as a systolic array of scoring stages. The darkened registers 326 hold the necessary comparison scores for the w-mer being processed in each pipeline stage. Although FIG. 15 shows a single comparison score being dropped for each scorer stage for ease of explanation, the preferred embodiment includes dropping two comparison scores per stage. There is also a plurality of pipeline scoring stages 330. The data flows from left to right on FIG. 15. The light registers 328 are pipeline calculation registers and are used to transfer the state of the recurrence from a previous scoring stage to the next with each column of registers containing a different w-mer in the pipeline 70. Initialization 322 is provided to the light registers 328, dark registers 326 and scoring stages 330.

Figure 16:
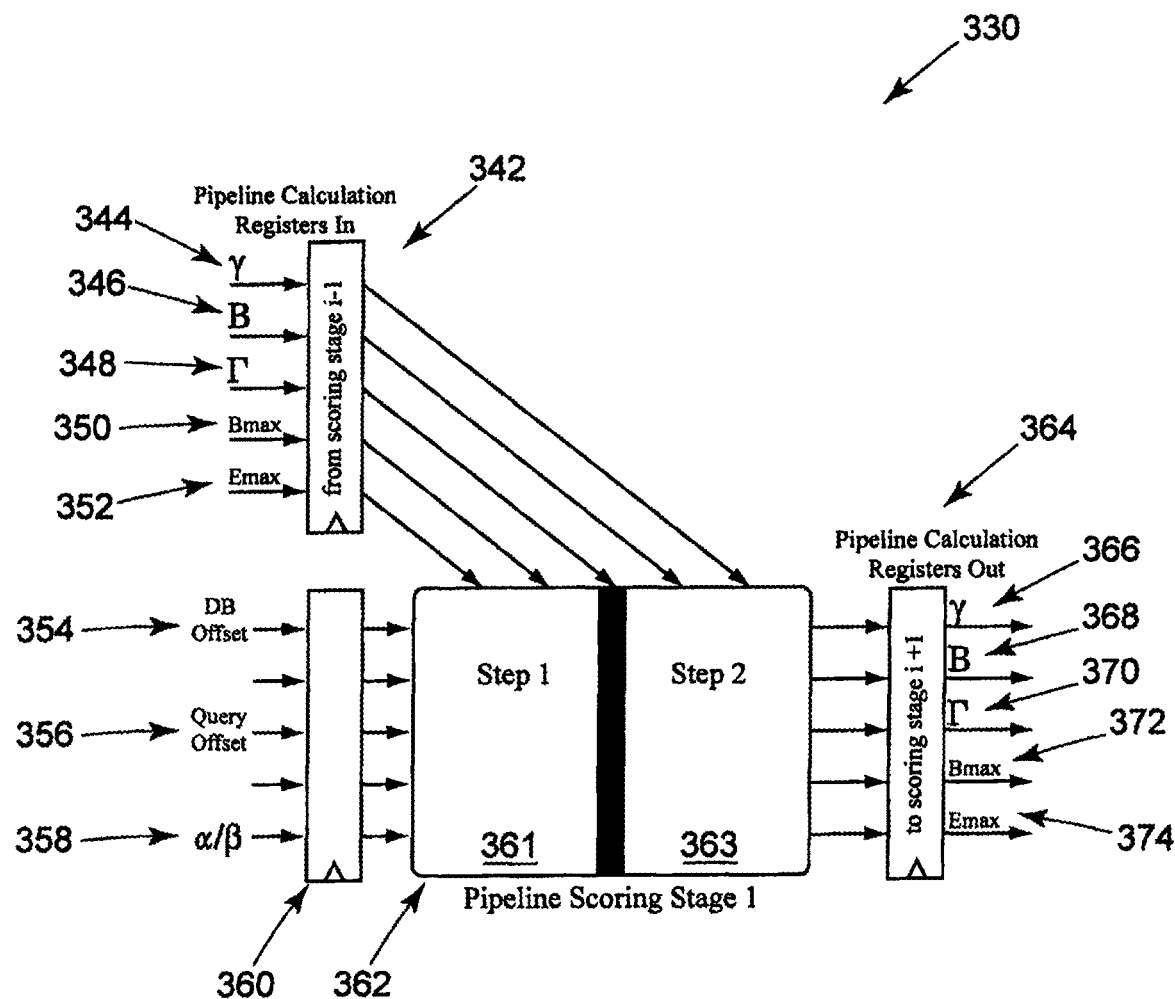
FIG. 16 is an illustrative, but nonlimiting, block diagram of a single two step scoring stage, as shown in FIG. 15, in accordance with a preferred, nonlimiting, illustrative embodiment of the present invention.

The interface of an individual scoring stage is generally indicated by numeral 330 and is shown in FIG. 16. The values shown entering the top of the scoring stage 330 are the state of dynamic programming recurrence propagated from the previous scoring stage. These values are read as input to a first register 342 and the results are stored in the output registers 364 shown on the right. Each scoring stage 362 in the pipeline 97 contains combinational logic to implement the dynamic programming recurrence shown in Lines 12-19 of the algorithm described in FIG. 12. This includes a value for γ indicated by numeral 344, a value for B indicated by numeral 346, a value for F indicated by numeral 348, a maximum value of B, i.e., $B_{max}$, indicated by numeral 350 and a maximum value of E, i.e., $E_{max}$, indicated by numeral 352.

The data entering from the left of the second register 360 are the comparison scores 358, i.e., α/β, and the database offset 354 and query offset 356 for a given w-mer, which are independent of the state of the recurrence. In order to sustain a high clock frequency design, each scoring stage computes only two iterations of the loop per clock cycle, resulting in $L_w/2$ scoring stages for a complete calculation. This provides step 1, indicated by numeral 361 and step 2, indicated by numeral 363, which implements two iterations of Lines 12 through 19 of the algorithm 66 shown in FIG. 12. This is merely an illustrative, but nonlimiting, number of loop iterations within a single stage since any number of loop iterations can be utilized. This tradeoff is preferred when contrasting area and speed utilizing the preferred and illustrative, but nonlimiting, hardware. Therefore, there are $L_w/2$ independent w-mers being processed simultaneously in the scoring stages 362 of the processor when the pipeline 70 is full.

The pipeline calculation registers output 364 that are provided to subsequent scoring stages, e.g., i+1. This includes a value for γ indicated by numeral 366, a value for B indicated by numeral 368, a value for F indicated by numeral 370, a maximum value of B, i.e., $B_{max}$, indicated by numeral 372 and a maximum value of E, i.e., $E_{max}$, indicated by numeral 374.

The final pipeline stage of the scoring module is the threshold comparator 99 that is shown in FIG. 13. The comparator takes the fully-scored segment and makes a decision to discard or keep the segment. This decision is based on the score of the alignment relative to a user-defined threshold T, as well as the position of the highest-scoring substring. If the maximum score is above the threshold, the segment is passed on. Additionally, if the maximal scoring substring intersects either boundary of the window, the segment is also passed on, regardless of the score. If neither condition holds, the substring of a predetermined length, i.e., segment, is discarded. The segments that are passed on are indicated by numeral 100 on FIG. 13.

In an optional and illustrative implementation, the ungapped extension prefilter 82, as shown in FIG. 13, utilizes approximately 38% of the logic cells and 27 BRAMs on a reconfigurable hardware such as, but not limited to, FPGAs (field programmable gate arrays) 74. An illustrative, but nonlimiting, example includes a Xilinx® Virtex-II 6000® series FPGA. Xilinx, Inc., is a Delaware Corporation, having a place of business at 2100 Logic Drive, San Jose, Calif. 95124-3400. This includes the infrastructure for moving data in and out of the reconfigurable hardware, e.g., FPGA, itself. The illustrative, but nonlimiting, current design runs at 96 MHz, processing one w-mer per clock. The full Mercury BLASTN design utilizes approximately 65% of the logic cells and 134 BRAMs.

There are many aspects to the performance of an ungapped extension prefilter 82, as shown in FIG. 13. First is the individual stage throughput. The ungapped extension stage (Stage 2*a*) 82 must run fast enough to not be a bottleneck in the overall pipeline 70. Second, the ungapped extension stage (Stage 2*a*) 82 must effectively filter as many w-mers as possible, since downstream stages are even more computationally expensive. Finally, the above must be achieved without inadvertently dropping a large percentage of the significant alignments (i.e., the false negative rate must be limited).

First, throughput performance for the ungapped extension stage alone is a function of data input rate. In an illustrative, but nonlimiting, example, the ungapped extension stage accepts one w-mer per clock and runs at 96 MHz. Hence the maximum throughput of the filter is one (1) input match/cycle times 96 MHz=96 Mmatches/second. This provides a speedup of twenty-five (25) over the software ungapped extension 82 executed on the previously described baseline system, as shown in FIG. 1. This analysis is based solely on modeling, based on assumed parameters and constraints, and actual results can vary.

Figure 17:
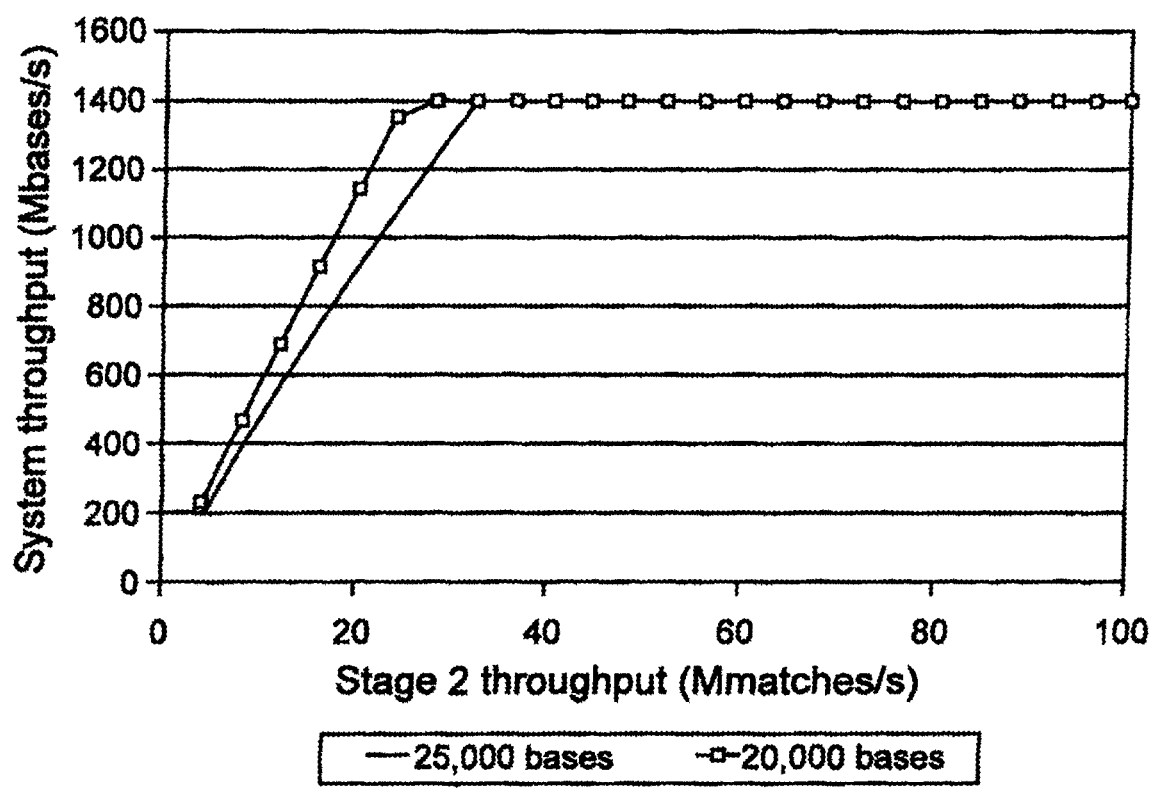
FIG. 17 is a graphical representation of throughput of an overall pipeline as a function of ungapped extension throughput for queries of sizes 20 kbases and 25 kbases.

FIG. 17 shows the application throughput (quantified by the ingest rate of the complete pipeline 70, in million bases per second) as a function of the performance attainable in the second stage (Stage 2) 56, as shown in FIG. 1, which is quantified by the ingest rate of the second stage (Stage 2) 56 alone, in million matches per second). FIG. 17 includes results for both 25,000-base double stranded queries and 20,000-base double stranded queries.

Figure 18:
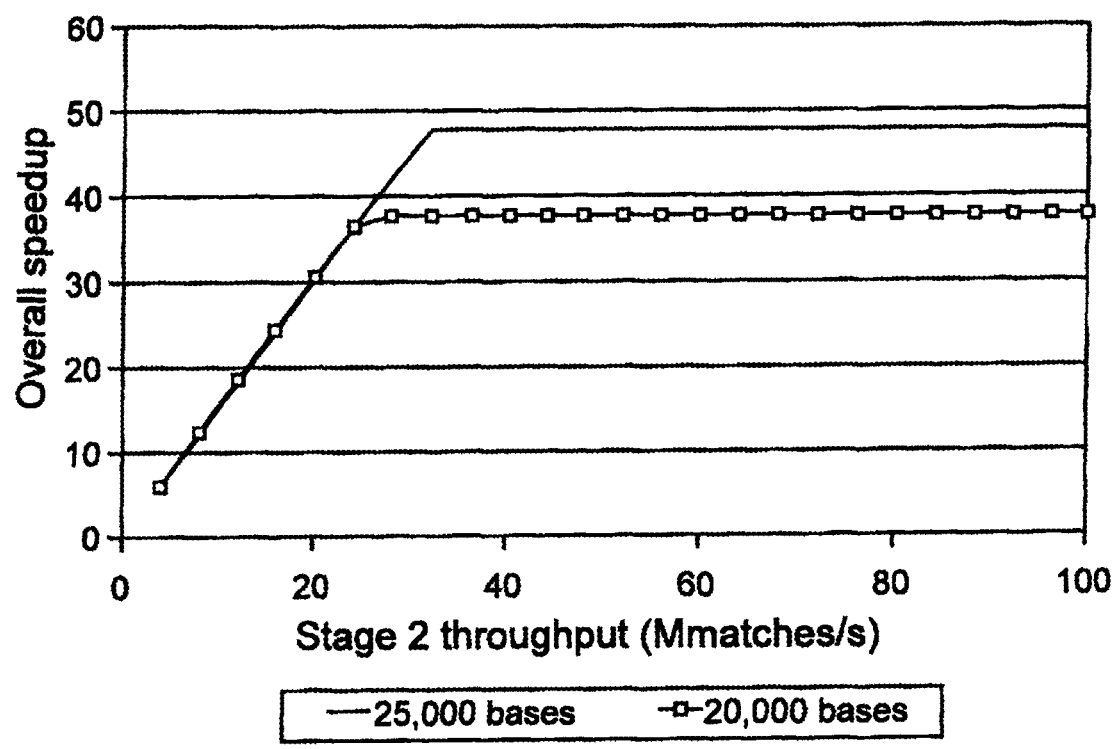
FIG. 18 is a graphical representation of speedup of an overall pipeline as a function of ungapped extension throughput for queries of sizes 20 kbases and 25 kbases with prefiltering in accordance with a preferred, nonlimiting, illustrative embodiment of the present invention.

FIG. 18 plots the resulting speedup versus throughput (for both query sizes) for the preferred embodiment of the present invention with a prefiltering stage (Stage 2*a*) 82 as shown on FIG. 11 relative to the software implementation. Once again, this analysis is based solely on modeling, based on assumed parameters and constraints, and actual results can vary. The software profiling shows, for 25,000-base queries, an average execution time for the second stage (Stage 2) 56 alone of 0.265 µs/match. This corresponds to a throughput of 3.8 Mmatches/s, plotted towards the left in FIGS. 17 and 18. As the performance of the second stage (Stage 2) 56 is increased, the overall pipeline 70 performance increases proportionately until the second stage (Stage 2) 56 is no longer the bottleneck stage.

To explore the impact this performance in the second stage (Stage 2) 56 has on the overall system, we return to the graphs of FIGS. 17 and 18. Above approximately 35 Mmatches/s, the overall system throughput is at its maximum rate of 1400 Mbases/s, with a speedup of forty-eight (48 times over that of software, e.g., NCBI BLASTN, for a 25,000-base query) and a speedup of thirty-eight (38 times over that of software, e.g., NCBI BLASTN, for a 20,000-base query).

There are two (2) parameters of ungapped extension that affect its sensitivity. The first parameter is the score threshold used, which affects the number of HSPs that are produced. The second parameter is the length of the window, which can affect the number of false negatives that are produced. The HSPs that have enough mismatches before the window boundary to be below the score threshold but have many matches immediately outside the boundary will be incorrectly rejected.

To evaluate the functional sensitivity of hardware ungapped extension 82, measurements were performed using an instrumented version of software, e.g., NCBI BLASTN. A software emulator of the new ungapped extension algorithm was placed in front of the standard ungapped extension stage, e.g., NCBI. Then, the statistics were gathered which show how many w-mers arrived at the ungapped extension prefilter stage 82, and how many passed.

These statistics were collected both for ungapped extension, the second stage (Stage 2) 56, FIG. 1, alone, e.g., NCBI BLASTN, and with the hardware emulator in place. The dataset was generated from the human and mouse genomes. The queries were statistically significant samples of various sizes (e.g., 10 kbase, 100 kbase, and 1 Mbase). The database stream was the mouse genome with low-complexity and repetitive sequences removed.

Figure 19:
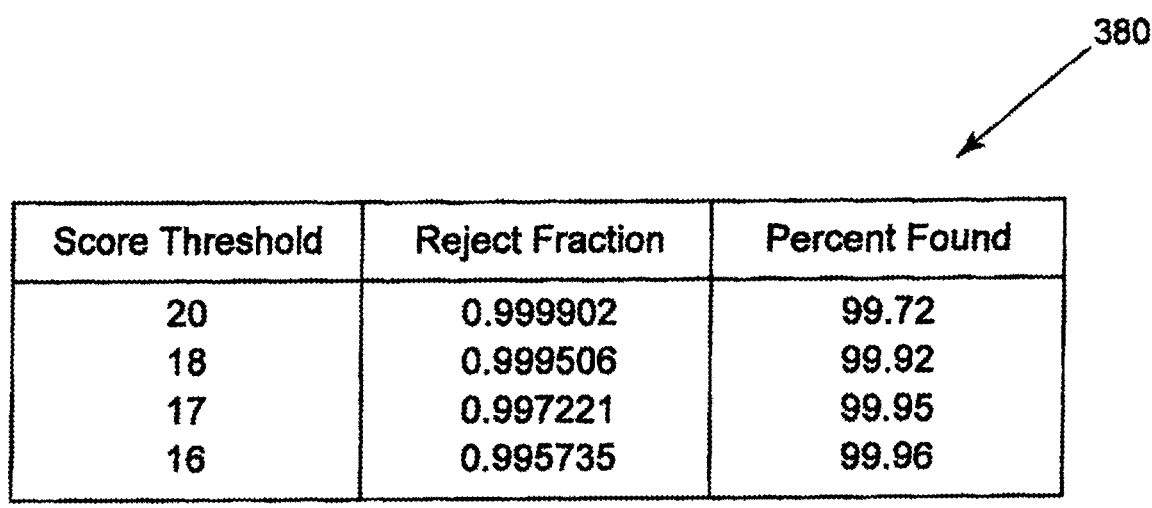
FIG. 19 is a table of sensitivity results for an illustrative, but nonlimiting, prefilter for the ungapped extension in accordance with a preferred, nonlimiting, illustrative embodiment of the present invention.

FIG. 19 is a table, generally indicated by numeral 380, which summarizes the results for a window size of 64 bases, which is the window size used in the illustrative, but nonlimiting hardware implementation. A score threshold of twenty (20) corresponds to the default value in ungapped extension or second stage (Stage 2) 82, FIG. 11, e.g., NCBI BLASTN. The reject fraction is the measured ratio of output HSPs over input w-mers. This value quantifies the effectiveness of the overall second stage (Stage 2) 82, FIG. 11, at filtering w-mers so they need not be processed in (Stage 2*b*) 84. The percent found is the percentage of gapped alignments present in the MERCURY BLAST's output relative to NCBI BLASTN output, as shown in FIG. 19.

Using a window length of 64 bases, the ungapped extension prefilter 82 is able to filter out between 99.5% and 99.99% of all its input. For instance, a threshold of seventeen (17) missed HSPs provides a good tradeoff between a high reject fraction while keeping the vast majority (99.95%) of the significant HSPs. This translates into five (5) missed HSPs out of 10,334 HSPs found by software system, e.g., NCBI BLAST.

Therefore, biosequence similarity searching can be accelerated practically by a pipeline 70 designed to filter high-speed streams of character data utilizing a performance-critical ungapped extension stage 56. The present invention is a highly parallel and pipelined implementation yields results comparable to those obtained from software, such as BLASTN, while running twenty-five times faster and enabling the entire accelerator to run approximately forty to fifty times faster.

For example, the techniques of the present invention can be used to implement word matching for seeded alignment searching techniques other than biological sequence similarity searching. Furthermore, the techniques of the present invention can also be applied to BLAST versions other than BLASTN, such as BLASTP, BLASTX, TBLASTN, and TBLASTX. Further still, the preferred embodiment has been described wherein the starting position of each matching w-mer within either the database sequence or the query sequence is determined by the various pipeline stages. However, it should be noted that these positions need not necessarily be the starting position. For example, the ending position or some intermediate position can also be used to identify the positions of the matching w-mers within the database and query sequences. These changes and modifications should be considered as alternative embodiments for the present invention, and the invention should be considered as limited only by the scope of the claims appended hereto and their legal equivalents.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "have," "having," "includes" and "including" and similar terms as used in the foregoing specification are used in the sense of "optional" or "may include" and not as "required." Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

What is claimed is:

1. An apparatus for comparing a first biosequence string with a second biosequence string to assess similarity between the first and second biosequence strings, the apparatus comprising:
    a field programmable gate array (FPGA) configured to (1) detect substrings of the second biosequence string that are matches to substrings of the first biosequence string and (2) map the detected substrings of the second biosequence string to corresponding positions in the first biosequence string where the detected substrings are located based on a data structure that links substrings of the first biosequence string to positions in the first biosequence string where the substrings of the first biosequence string are located.

2. The apparatus of claim 1 further comprising a memory for storing the data structure.

3. The apparatus of claim 2 wherein the memory is resident on the FPGA.

4. The apparatus of claim 2 wherein the memory is off-chip from the FPGA.

5. The apparatus of claim 1 wherein the data structure comprises a hash table.

6. The apparatus of claim 1 wherein the matches include false positive matches with respect to the first biosequence string.

7. The apparatus of claim 6 wherein the FPGA comprises a Bloom filter to detect substrings of the second biosequence string that are possible matches to substrings of the first biosequence string.

8. The apparatus of claim 6 wherein the map operation eliminates a plurality of false positives from the detected substrings, wherein the eliminated false positives correspond to detected substrings that are not linked by the data structure to positions in the first biosequence string.

9. The apparatus of claim 8 wherein the data structure comprises a hash table, and wherein the eliminated false positives are detected substrings of the second biosequence string that are linked to empty entries in the hash table.

10. The apparatus of claim 1 wherein the FPGA is configured as a multistage pipeline that includes pipeline stages for performing the detect and map operations on a stream of the second biosequence string.

11. The apparatus of claim 10 wherein the multistage pipeline provides BLAST Stage 1 operations.

12. The apparatus of claim 1 wherein the first biosequence string is a query sequence of DNA bases, and wherein the second biosequence string is a database sequence of DNA bases.

13. The apparatus of claim 1 wherein the FPGA further comprises an ungapped extension filter, and wherein the FPGA is further configured to apply the detected and mapped substrings to the ungapped extension filter.

14. The apparatus of claim 13 wherein the FPGA is further configured to identify (1) windows of the second biosequence string around the detected and mapped substrings and (2) corresponding windows of the first biosequence string around the mapped positions for the detected and mapped sub strings.

15. The apparatus of claim 14 wherein the ungapped extension filter is configured to (1) quantify a similarity between pairs of longer substrings of the first and second biosequence strings within the identified corresponding windows and (2) identify the pairs for which the quantified similarity is above a threshold.

16. The apparatus of claim 1 wherein the FPGA is further configured to (1) generate a plurality of partially overlapping substrings of the second biosequence string and (2) process the partially overlapping substrings to detect the matches to substrings of the first biosequence string.

17. An apparatus for comparing a first biosequence string with a second biosequence string to assess similarity between the first and second biosequence strings, the apparatus comprising:
    a field programmable gate array (FPGA) configured to process a stream of the second biosequence string through a pipeline resident on the FPGA, wherein the pipeline is configured to (1) map positions within the first and second biosequence strings to each other based where matches exist within the first and second biosequence strings between substrings of the first and second biosequence strings and (2) based on the mapped positions of the first and second biosequence strings, find an alignment between longer substrings of the first and second biosequence substrings for which a similarity between the aligned longer substrings is above a threshold.

18. The apparatus of claim 17 wherein the first biosequence string is a query sequence of DNA bases, and wherein the second biosequence string is a database sequence of DNA bases.

19. An apparatus for comparing a first biosequence string with a second biosequence string to assess similarity between the first and second biosequence strings, the apparatus comprising:
    a field programmable gate array (FPGA), wherein the FPGA is configured to:
        detect a substring of the second biosequence string that matches a substring of the first biosequence string;
        map the detected substring of the second biosequence string to a position in the first biosequence string where the detected substring is located;
        perform a comparison between a longer substring of the second biosequence string and a corresponding longer substring of the first biosequence substring, wherein the longer substring of the second biosequence string encompasses the detected and mapped substring, and wherein the corresponding longer substring of the first biosequence string encompasses the mapped position for the detected and mapped substring;

quantify a similarity between the longer substrings of the first and second biosequence strings based on the comparison; and perform the detect, map, comparison, and quantify operations with respect to a plurality of different substrings of the first and second biosequence strings.

20. The apparatus of claim 19 wherein the FPGA is further configured to perform the comparison by:
identifying (i) a window of the second biosequence string that encompasses the detected and mapped sub string and (ii) a corresponding window of the first biosequence string that encompasses the mapped position for the detected and mapped substring; and
comparing, as a pair, longer substrings of the first and second biosequence strings that are within the identified corresponding windows to quantify the similarity between the pair.

21. The apparatus of claim 19 wherein the FPGA is further configured to identify pairs of the longer substrings for which their quantified similarities is above a threshold.

22. The apparatus of claim 19 wherein the FPGA is further configured to quantify the similarities based on a plurality of scoring stages.

23. The apparatus of claim 19 wherein the matches include false positive matches with respect to the first biosequence string.

24. The apparatus of claim 23 wherein the FPGA comprises a Bloom filter to detect substrings of the second biosequence string that are possible matches to substrings of the first biosequence string.

25. The apparatus of claim 24 wherein the map operations eliminate a plurality of false positives from the detected substrings.

26. The apparatus of claim 19 wherein the FPGA is configured as a multistage pipeline that includes pipeline stages for a parallel performance of the detect, map, and comparison operations on a stream of the second biosequence string from which the substrings of the second biosequence string are derived.

27. The apparatus of claim 19 wherein the first biosequence string is a query sequence of DNA bases, and wherein the second biosequence string is a database sequence of DNA bases.

28. The apparatus of claim 19 wherein the FPGA comprises an ungapped extension filter that performs the compare and quantify operations.

29. A method for comparing a first biosequence string with a second biosequence string to assess similarity between the first and second biosequence strings, the method comprising:
a field programmable gate array (FPGA) comparing a first substring of the first biosequence string with a first substring of the second biosequence string to quantify a similarity between the first substring of the first biosequence string and the first substring of the second biosequence string;
the FPGA seeding the comparing step by detecting a position within the first biosequence substring and a position within the second biosequence substring which correspond to second substrings of the first and second biosequence strings respectively that match each other, wherein the first substrings are longer than the second substrings; and
the FPGA performing the seeding and comparing steps with respect to a plurality of different substrings of the first and second biosequence strings.

30. The method of claim 29 wherein the first biosequence string is a query sequence of DNA bases, and wherein the second biosequence string is a database sequence of DNA bases.

* * * * *